(12) United States Patent
Sahiner et al.

(10) Patent No.: US 12,171,779 B2
(45) Date of Patent: Dec. 24, 2024

(54) REGULATED DRUG DELIVERY VIA CONTROLLED DEGRADABLE CHONDROITIN SULFATE PARTICLES

(71) Applicant: UNIVERSITY OF SOUTH FLORIDA, Tampa, FL (US)

(72) Inventors: Nurettin Sahiner, Tampa, FL (US); Ramesh Ayyala, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/077,533

(22) Filed: Dec. 8, 2022

(65) Prior Publication Data

US 2023/0172970 A1 Jun. 8, 2023

Related U.S. Application Data

(60) Provisional application No. 63/265,101, filed on Dec. 8, 2021.

(51) Int. Cl.
*A61K 31/737* (2006.01)
*A61K 9/00* (2006.01)
*A61K 9/50* (2006.01)

(52) U.S. Cl.
CPC .......... *A61K 31/737* (2013.01); *A61K 9/0014* (2013.01); *A61K 9/0048* (2013.01); *A61K 9/5015* (2013.01)

(58) Field of Classification Search
CPC ............... A61K 31/737; A61K 9/0014; A61K 9/0048; A61K 9/5015; A61K 9/1652; A61K 9/5036; A61K 9/5161; A61K 31/7036
USPC ........................................................ 514/54
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,893,397 A | 4/1999 | Peterson et al. |
| 5,993,412 A | 11/1999 | Deily et al. |
| 2011/0256059 A1* | 10/2011 | Sanchez Barreiro .. A61Q 19/00 424/9.1 |
| 2020/0190225 A1* | 6/2020 | Gravett ............... A61L 26/0066 |

FOREIGN PATENT DOCUMENTS

| | | |
|---|---|---|
| WO | 1997013537 | 4/1997 |
| WO | 1997037705 | 10/1997 |
| WO | 1999034850 | 7/1999 |

OTHER PUBLICATIONS

Wyss, P.P.; Lamichhane, S.P.; Abed, A.; Vonwil, D.; Kretz, O.; Huber, T.B.; Sarem, M.; Shastri, V.P. Renal clearance of polymeric nanoparticles by mimicry of glycan surface of viruses. Biomaterials 2020, 230, 119643, doi: 10.1016/j.biomaterials.2019.119643.
Fajardo, A.R.; Lopes, L.C.; Caleare, A.O.; Britta, E.A.; Nakamura, C. V.; Rubira, A.F.; Muniz, E.C. Silver sulfadiazine loaded chitosan/chondroitin sulfate films for a potential wound dressing application. Mater. Sci. Eng. C 2013, 33, 588-595, doi:10.1016/j.msec.2012.09.025.
Lopez-Moya, M.; Melgar-Lesmes, P.; Kolandaivelu, K.; De La Torre Hernández, J.M.; Edelman, E.R.; Balcells, M. Optimizing Glutaraldehyde-Fixed Tissue Heart Valves with Chondroitin Sulfate Hydrogel for Endothelialization and Shielding against Deterioration. Biomacromolecules 2018, 19, 1234-1244, doi: 10.1021/acs.biomac.8b00077.
Cao, J.F.; Xu, W.; Zhang, Y.Y.; Shu, Y.; Wang, J.H. Chondroitin sulfate-functionalized 3D hierarchical flower-type mesoporous silica with a superior capacity for selective isolation of low density lipoprotein. Anal. Chim. Acta 2020, 1104, 78-86, doi: 10.1016/j.aca.2019.12.075.
Zhao, S.; Zhou, Y.; Wei, L.; Chen, L. Low fouling strategy of electrochemical biosensor based on chondroitin sulfate functionalized gold magnetic particle for voltammetric determination of mycoplasma ovipneumonia in whole serum. Anal. Chim. Acta 2020, 1126, 91-99, doi: 10.1016/j.aca.2020.06.015.
Grazioli, G.; Silva, A.F.; Souza, J.F.; David, C.; Diehl, L.; Sousa-Neto, M.D.; Cava, S.S.; Fajardo, A.R.; Moraes, R.R. Synthesis and characterization of poly(vinyl alcohol)/chondroitin sulfate composite hydrogels containing strontium-doped hydroxyapatite as promising biomaterials. J. Biomed. Mater. Res.—Part A 2021, 109, 1160-1172, doi: 10.1002/jbm.a.37108.
Ronca, F.; Palmieri, L.; Panicucci, P.; Ronca, G. Anti-inflammatory activity of chondroitin sulfate. Osteoarthr. Cartil. 1998, 6, 14-21, doi: 10.1016/S1063-4584(98)80006-X.

(Continued)

*Primary Examiner* — Yih-Horng Shiao
*Assistant Examiner* — Jaret J Crews
(74) *Attorney, Agent, or Firm* — Meunier Carlin & Curfman LLC

(57) ABSTRACT

Disclosed herein are crosslinked chondroitin sulfate particles crosslinked chondroitin sulfate particle polyelectrolytes. The particles are useful in drug delivery applications. The particles may be used to treat various conditions, including bacterial and fungal infections.

18 Claims, 16 Drawing Sheets

(56) References Cited

OTHER PUBLICATIONS

Fajardo, A.R.; Guerry, A.; Britta, E.A.; Nakamura, C. V.; Muniz, E.C.; Borsali, R.; Halila, S. Sulfated glycosaminoglycan-based block copolymer: Preparation of biocompatible chondroitin sulfate-b-poly(lactic acid) micelles. Biomacromolecules 2014, 15, 2691-2700, doi: 10.1021/bm5005355.

Campo, G.M.; Avenoso, A.; Campo, S.; Ferlazzo, A.M.; Calatroni, A. Antioxidant Activity of Chondroitin Sulfate. In; 2006; pp. 417-431.

Chen, A.L.; Ni, H.C.; Wang, L.F.; Chen, U.S. Biodegradable amphiphilic copolymers based on poly($\zeta$-caprolactone)-graft chondroitin sulfate as drug carriers. Biomacromolecules 2008, 9, 2447-2457, doi: 10.1021/bm800485x.

Hammoudeh, S.M.; Hammoudeh, A.M.; Hamoudi, R. High-throughput quantification of the effect of DMSO on the viability of lung and breast cancer cells using an easy-to-use spectrophotometric trypan blue-based assay. Histochem. Cell Biol. 2019, 152, 75-84, doi: 10.1007/s00418-019-01775-7.

Zhao, L.; Liu, M.; Wang, J.; Zhai, G. Chondroitin sulfate-based nanocarriers for drug/gene delivery. Carbohydr. Polym. 2015, 133, 391-399, doi:10.1016/j.carbpol.2015.07.063.

Benito-Arenas, R.; Zárate, S.G.; Revuelta, J.; Bastida, A. Chondroitin sulfate- degrading enzymes as tools for the development of new pharmaceuticals. Catalysts 2019, 9, doi: 10.3390/catal9040322.

Shi, X.; Yang, X.; Liu, M.; Wang, R.; Qiu, N.; Liu, Y.; Yang, H.; Ji, J.; Zhai, G. Chondroitin sulfate-based nanoparticles for enhanced chemo-photodynamic therapy overcoming multidrug resistance and lung metastasis of breast cancer. Carbohydr. Polym. 2021, 254, 117459, doi: 10.1016/j.carbpol.2020.117459.

Talib, S.; Ahmed, N.; Khan, D.; Khan, G.M.; Rehman, A. ur Chitosan-chondroitin based artemether loaded nanoparticles for transdermal drug delivery system. J. Drug Deliv. Sci. Technol. 2021, 61, 102281, doi: 10.1016/j.jddst.2020.102281.

Rodrigues, S.; da Costa, A.M.R.; Flórez-Fernández, N.; Torres, M.D.; Faleiro, M.L.; Buttini, F.; Grenha, A. Inhalable spray-dried chondroitin sulphate microparticles: Effect of different solvents on particle properties and drug activity. Polymers (Basel). 2020, 12, 1-13, doi: 10.3390/polym12020425.

Rodrigues, S.; Cunha, L.; Kollan, J.; Neumann, P.R.; Rosa da Costa, A.M.; Dailey, L.A.; Grenha, A. Cytocompatibility and cellular interactions of chondroitin sulfate microparticles designed for inhaled tuberculosis treatment. Eur. J. Pharm. Biopharm. 2021, 163, 171-178, doi:10.1016/j.ejpb.2021.04.001.

Chen, L.; Li, J.; Bi, X.; Ji, J.; Wang, L.; Cheng, J. Chondroitin sulfate micro granules embedded with oligochitosan-calcium complexes for potential osteoporosis prevention. J. Funct. Foods 2022, 90, 104984, doi: 10.1016/j.jff.2022.104984.

Pal, D.; Saha, S. Chondroitin: A natural biomarker with immense biomedical applications. RSC Adv. 2019, 9, 28061-28077, doi: 10.1039/c9ra05546k.

Li, S.; Ma, F.; Pang, X.; Tang, B.; Lin, L. Synthesis of chondroitin sulfate magnesium for osteoarthritis treatment. Carbohydr. Polym. 2019, 212, 387-394, doi: 10.1016/j.carbpol.2019.02.061.

Wu, G.; Ma, F.; Xue, Y.; Peng, Y.; Hu, L.; Kang, X.; Sun, Q.; Ouyang, D.F.; Tang, B.; Lin, L. Chondroitin sulfate zinc with antibacterial properties and anti-inflammatory effects for skin wound healing. Carbohydr. Polym. 2022, 278, 118996, doi: 10.1016/j.carbpol.2021.118996.

Xiong, M.H .; Bao, Y .; Yang, X.Z .; Zhu, Y.H.; Wang, J. Delivery of antibiotics with polymeric particles. Adv. Drug Deliv. Rev. 2014, 78, 63-76, doi: 10.1016/j.addr.2014.02.002.

Sahiner, N.; Suner, S.S.; Ayyala, R.S. Mesoporous, degradable hyaluronic acid microparticles for sustainable drug delivery application. Colloids Surfaces B Biointerfaces 2019, 177, 284-293, doi: 10.1016/j.colsurfb.2019.02.015.

Gebreel, R.M.; Edris, N.A.; Elmofty, H.M.; Tadros, M.I.; El-Nabarawi, M.A.; Hassan, D.H. Development and characterization of PLGA nanoparticle-laden hydrogels for sustained ocular delivery of norfloxacin in the treatment of pseudomonas keratitis: An experimental study. Drug Des. Devel. Ther. 2021, 15, 399-418, doi: 10.2147/DDDT.S293127.

Brooks, A.E.; Brooks, B.D.; Davidoff, S.N.; Hogrebe, P.C.; Fisher, M.A.; Grainger, D.W. Polymer-controlled release of tobramycin from bone graft void filler. Drug Deliv. Transl. Res. 2013, 3, 518-530, doi: 10.1007/s13346-013-0155-x.

Dubald, M.; Bourgeois, S.; Andrieu, V.; Fessi, H. Ophthalmic drug delivery systems for antibiotherapy—A review. Pharmaceutics 2018, 10, doi: 10.3390/pharmaceutics10010010.

Cavalli, R.; Bargoni, A.; Podio, V.; Muntoni, E.; Zara, G.P.; Gasco, M.R. Duodenal administration of solid lipid nanoparticles loaded with different percentages of tobramycin. J. Pharm. Sci. 2003, 92, 1085-1094, doi: 10.1002/jps.10368.

Pecora, T.M.G.; Ragazzo, B.; Bertin, W.; Ragonese, A.; Mascagni, M.; Maffei, P.; Pignatello, R. Rheological behavior of a new mucoadhesive oral formulation based on sodium chondroitin sulfate, xyloglucan and glycerol. J. Funct. Biomater. 2021, 12, doi: 10.3390/jfb12020028.

Suchaoin, W.; Bonengel, S.; Grießinger, J.A.; Pereira De Sousa, I.; Hussain, S.; Huck, C.W.; Bernkop-Schnürch, A. Novel bioadhesive polymers as intra-articular agents: Chondroitin sulfate-cysteine conjugates. Eur. J. Pharm. Biopharm. 2016, 101, 25-32, doi:10.1016/j.ejpb.2016.01.006.

Abdullah, T.; Ibrahim, N.; Warsi, M. Chondroitin sulfate-chitosan nanoparticles for ocular delivery of bromfenac sodium: Improved permeation, retention, and penetration. Int. J. Pharm. Investig. 2016, 6, 96, doi: 10.4103/2230-973x.177823.

Ng, W.K.; Tam, K.C.; Jenkins, R.D. Evaluation of intrinsic viscosity measurements of hydrophobically modified polyelectrolyte solutions. Eur. Polym. J. 1999, 35, 1245-1252, doi: 10.1016/S0014-3057(98)00199-2.

Alatorre-Meda, M.; Taboada, P.; Sabín, J .; Krajewska, B.; Varela, L.M.; Rodríguez, J.R. DNA-chitosan complexation: A dynamic light scattering study. Colloids Surfaces A Physicochem. Eng. Asp. 2009, 339, 145-152, doi:10.1016/j.colsurfa.2009.02.014.

Fajardo, A.R.; Silva, M.B.; Lopes, L.C.; Piai, J.F.; Rubira, A.F.; Muniz, E.C. Hydrogel based on an alginate-Ca2+/chondroitin sulfate matrix as a potential colon-specific drug delivery system. RSC Adv. 2012, 2, 11095-11103, doi: 10.1039/c2ra20785k.

Zhu, L.; Wang, J. Fast determination of tobramycin by reversed-phase ion-pair high performance liquid chromatography with a refractive index detector. Front. Chem. Sci. Eng. 2013, 7, 322-328, doi: 10.1007/s11705-013-1348-z.

Sahiner, N.; Suner, S.S.; Kurt, S.B.; Can, M.; Ayyala, R.S. Ha particles as resourceful cancer, steroidal and antibiotic drug delivery device with sustainable and multiple drug release capability. J. Macromol. Sci. Part A Pure Appl. Chem. 2021, 58, 145-155, doi: 10.1080/10601325.2020.1832518.

Mosmann, T. Rapid colorimetric assay for cellular growth and survival: Application to proliferation and cytotoxicity assays. J. Immunol. Methods 1983, 65, 55-63, doi: 10.1016/0022-1759(83)90303-4.

Riss, T.L.; Moravec, R.A.; Niles, A.L.; Duellman, S.; Benink, H.A.; Worzella, T.J.; Minor, L. Cell Viability Assays. Assay Guid. Man. 2004, 1-25.

Foot, M.; Mulholland, M. Classification of chondroitin sulfate A, chondroitin sulfate C, glucosamine hydrochloride and glucosamine 6 sulfate using chemometric techniques. J. Pharm. Biomed. Anal. 2005, 38, 397-407, doi: 10.1016/j.jpba.2005.01.026.

Sy, A.; Srinivasan, M.; Mascarenhas, J.; Lalitha, P.; Rajaraman, R.; Ravindran, M.; Oldenburg, C.E.; Ray, K.J.; Glidden, D.; Zegans, M.E.; et al. Pseudomonas aeruginosa keratitis: Outcomes and response to corticosteroid treatment. Investig. Ophthalmol. Vis. Sci. 2012, 53, 267-272, doi: 10.1167/iovs.11-7840.

Brogden, R.N.; Pinder, R.M.; Sawyer, P.R.; Speight, T.M.; Avery, G.S. Tobramycin: A Review of its Antibacterial and Pharmacokinetic Properties and Therapeutic Use. Drugs 1976, 12, 166-200, doi: 10.2165/00003495-197612030- 00002.

Begg, E.J.; Barclay, M.L. Aminoglycosides—50 years on. Br. J. Clin. Pharmacol. 1995, 39, 597-603.

(56) References Cited

OTHER PUBLICATIONS

Suner, S.S.; Ari, B.; Demirci, S.; Sahiner, N. Tunable Biopolymeric Drug Carrier Nanovehicles and Their Safety. In Nano Medicine and Nano Safety; Springer Singapore: Singapore, 2020; pp. 405-432.

Danaei, M.; Dehghankhold, M.; Ataei, S.; Hasanzadeh Davarani, F.; Javanmard, R.; Dokhani, A.; Khorasani, S.; Mozafari, M.R. Impact of particle size and polydispersity index on the clinical applications of lipidic nanocarrier systems. Pharmaceutics 2018, 10, doi: 10.3390/pharmaceutics10020057.

Dong, R.; Guo, B. Smart wound dressings for wound healing. Nano Today 2021, 41, 101290, doi: 10.1016/j.nantod.2021.101290.

Liang, Y.; He, J.; Guo, B. Functional Hydrogels as Wound Dressing to. 2021, doi: 10.1021/acsnano.1c04206.

Liang, Y.; Li, M.; Yang, Y.; Qiao, L.; Xu, H.; Guo, B. pH/Glucose Dual Responsive Metformin Release Hydrogel Dressings with Adhesion and Self-Healing via Dual-Dynamic Bonding for Athletic Diabetic Foot Wound Healing. 2022, doi: 10.1021/acsnano.1c11040.

Deacon, J.; Abdelghany, S.M.; Quinn, D.J.; Schmid, D.; Megaw, J.; Donnelly, R.F.; Jones, D.S.; Kissenpfennig, A.; Elborn, J.S.; Gilmore, B.F.; et al. Antimicrobial efficacy of tobramycin polymeric nanoparticles for Pseudomonas aeruginosa infections in cystic fibrosis: Formulation, characterisation and functionalisation with dornase alfa (DNase). J. Control. Release 2015, 198, 55-61.

Postic, I.; Sheardown, H. Altering the release of tobramycin by incorporating poly(ethylene glycol) into model silicone hydrogel contact lens materials. J. Biomater. Sci. Polym. Ed. 2019, 30, 1115-1141, doi: 10.1080/09205063.2019.1580663.

Hadinoto, K.; Cheow, W.S. Nano-antibiotics in chronic lung infection therapy against Pseudomonas aeruginosa. Colloids Surfaces B Biointerfaces 2014, 116, 772-785, doi:10.1016/j.colsurfb.2014.02.032.

Sharma, U.K.; Verma, A.; Prajapati, S.K.; Pandey, H.; Pandey, A.C. In vitro, in vivo and pharmacokinetic assessment of amikacin sulphate laden polymeric nanoparticles meant for controlled ocular drug delivery. Appl. Nanosci. 2015, 5, 143-155, doi:10.1007/s13204-014-0300-y.

McCormick, C.; Caballero, A.; Tang, A.; Balzli, C.; Song, J.; O'Callaghan, R. Effectiveness of a new tobramycin (0.3%) and dexamethasone (0.05%) formulation in the treatment of experimental Pseudomonas keratitis. Curr. Med. Res. Opin. 2008, 24, 1569-1575, doi: 10.1185/03007990802079877.

Miranda, C.S.; Antunes, J.C.; Homem, N.C.; Felgueiras, H.P. Controlled Release of Cinnamon Leaf Oil from Chitosan Microcapsules Embedded within a Sodium Alginate / Gelatin Hydrogel-Like Film for Pseudomonas aeruginosa Elimination +. 2021.

Ginalska, G.; Kowalczuk, D.; Osińska, M. Amikacin-loaded vascular prosthesis as an effective drug carrier. Int. J. Pharm. 2007, 339, 39-46, doi:10.1016/j.ijpharm.2007.02.016.

Han, J.; Guo, X.; Lei, Y.; Dennis, B.S.; Wu, S.; Wu, C. Synthesis and characterization of selenium-chondroitin sulfate nanoparticles. Carbohydr. Polym. 2012, 90, 122-126, doi: 10.1016/j.carbpol.2012.04.068.

Cazorla-Luna, R.; Martín-Illana, A.; Notario-Pérez, F.; Ruiz-Caro, R.; Veiga, M.D. Naturally occurring polyelectrolytes and their use for the development of complex-based mucoadhesive drug delivery systems: An overview. Polymers (Basel). 2021, 13, doi: 10.3390/polym13142241.

Hermal, F.; Frisch, B.; Specht, A.; Bourel-Bonnet, L.; Heurtault, B. Development and characterization of layer-by-layer coated liposomes with poly(L-lysine) and poly(L-glutamic acid) to increase their resistance in biological media. Int. J. Pharm. 2020, 586, 119568, doi: 10.1016/j.ijpharm.2020.119568.

She, Z.; Wang, C.; Li, J.; Sukhorukov, G.B.; Antipina, M.N. Encapsulation of Basic Fibroblast Growth Factor by Polyelectrolyte Multilayer Microcapsules and Its Controlled Release for Enhancing Cell Proliferation. Biomacromolecules 2012, 13, 2174-2180, doi: 10.1021/bm3005879.

Balabushevich, N.G.; Larionova, N.I. Fabrication and Characterization of Polyelectrolyte Microparticles with Protein. Biochem. 2004, 69, 757-762, doi: 10.1023/B:BIRY.0000040200.61663.01.

Dash, P.; Thirumurugan, S.; Hu, C.C.; Wu, C.J.; Shih, S.J.; Chung, R.J. Preparation and characterization of polyelectrolyte multilayer coatings on 316L stainless steel for antibacterial and bone regeneration applications. Surf. Coatings Technol. 2022, 435, 128254, doi: 10.1016/j.surfcoat.2022.128254.

Delvart, A.; Moreau, C.; Cathala, B. Dextrans and dextran derivatives as polyelectrolytes in layer-by-layer processing materials—A review. Carbohydr. Polym. 2022, 293, doi: 10.1016/j.carbpol.2022.119700.

Chen, J.; Liu, W.; Liu, C.-M.; Li, T.; Liang, R.-H.; Luo, S.-J. Pectin Modifications: A Review. Crit. Rev. Food Sci. Nutr. 2015, 55, 1684-1698, doi: 10.1080/10408398.2012.718722.

Khalid, S.; Abbas, G.; Hanif, M.; Shah, S.; Shah, S.N.H.; Jalil, A.; Yaqoob, M.; Ameer, N.; Anum, A. Thiolated sodium alginate conjugates for mucoadhesive and controlled release behavior of metformin microspheres. Int. J. Biol. Macromol. 2020, 164, 2691-2700, doi: 10.1016/j.ijbiomac.2020.08.116.

Sahiner, N.; Umut, E.; Suner, S.S.; Sahiner, M.; Culha, M.; Ayyala, R.S. Hyaluronic acid (HA)-Gd(III) and HA-Fe(III) microgels as MRI contrast enhancing agents. Carbohydr. Polym. 2022, 277, 118873, doi: 10.1016/j.carbpol.2021.118873.

Malviya, R., Exploration of neem gum-chitosan and kheri gum-chitosan polyelectrolyte complex based film for transdermal delivery of protein/peptide. Biointerface Res. Appl. Chem. 2020, 10, 5860-5868, doi: 10.33263/BRIAC104.860868.

Bueno, P.V.A.; Souza, P.R.; Follmann, H.D.M.; Pereira, A.G.B.; Martins, A.F.; Rubira, A.F.; Muniz, E.C. N,N-Dimethyl chitosan/heparin polyelectrolyte complex vehicle for efficient heparin delivery. Int. J. Biol. Macromol. 2015, 75, 186-191, doi:10.1016/j.ijbiomac.2015.01.030.

Sharma, S.; Swetha, K.L.; Roy, A. Chitosan-Chondroitin sulfate based polyelectrolyte complex for effective management of chronic wounds. Int. J. Biol. Macromol. 2019, 132, 97-108, doi: 10.1016/j.ijbiomac.2019.03.186.

Guarnizo-Herrero, V.; Torrado-Salmerón, C.; Pabón, N.S.T.; Durán, G.T.; Morales, J.; Torrado-Santiago, S. Study of different chitosan/sodium carboxymethyl cellulose proportions in the development of polyelectrolyte complexes for the sustained release of clarithromycin from matrix tablets. Polymers (Basel). 2021, 13, doi: 10.3390/polym13162813.

Uspenskaya, E. V.; Syroeshkin, A. V.; Pleteneva, T. V.; Kazimova, I. V.; Grebennikova, T. V.; Fedyakina, I.T.; Lebedeva, V. V.; Latyshev, O.E.; Eliseeva, O. V.; Larichev, V.F.; et al. Nanodispersions of polyelectrolytes based on humic substances: Isolation, physicochemical characterization and evaluation of biological activity. Pharmaceutics 2021, 13, doi: 10.3390/pharmaceutics13111954.

Panda, P.K.; Yang, J.M.; Chang, Y.H. Preparation and characterization of ferulic acid-modified water soluble chitosan and poly (γ-glutamic acid) polyelectrolyte films through layer-by-layer assembly towards protein adsorption. Int. J. Biol. Macromol. 2021, 171, 457-464, doi: 10.1016/j.ijbiomac.2020.12.226.

Bravo-Anaya, L.M.; Fernández-Solís, K.G.; Rosselgong, J.; Nano-Rodríguez, J.L.E.; Carvajal, F.; Rinaudo, M. Chitosan-DNA polyelectrolyte complex: Influence of chitosan characteristics and mechanism of complex formation. Int. J. Biol. Macromol. 2019, 126, 1037-1049, doi: 10.1016/j.ijbiomac.2019.01.008.

Kulkarni, A.D.; Vanjari, Y.H.; Sancheti, K.H.; Patel, H.M.; Belgamwar, V.S.; Surana, S.J.; Pardeshi, C. V. Polyelectrolyte complexes: mechanisms, critical experimental aspects, and applications. Artif. Cells, Nanomedicine Biotechnol. 2016, 44, 1615-1625, doi: 10.3109/21691401.2015.1129624.

Da Câmara, P.C.F.; Balaban, R.C.; Hedayati, M.; Popat, K.C.; Martins, A.F.; Kipper, M.J. Novel cationic tannin/glycosaminoglycan-based polyelectrolyte multilayers promote stem cells adhesion and proliferation. RSC Adv. 2019, 9, 25836-25846, doi: 10.1039/C9RA03903A.

Ishihara, M.; Kishimoto, S.; Nakamura, S.; Sato, Y.; Hattori, H. Polyelectrolyte Complexes of Natural Polymers and Their Biomedical Applications. Polymers (Basel). 2019, 11, 672, doi: 10.3390/polym11040672.

(56) References Cited

OTHER PUBLICATIONS

Briones, X.; Villalobos, V.; Queneau, Y.; Danna, C.S.; Muñoz, R.; Ríos, H.E.; Pavez, J.; Páez, M.; Cabrera, R.; Tamayo, L.; et al. Surfaces based on amino acid functionalized polyelectrolyte films towards active surfaces for enzyme immobilization. Mater. Sci. Eng. C 2019, 104, 109938, doi:10.1016/j.msec.2019.109938.

Kuo, Y.J.; Chen, C.H.; Dash, P.; Lin, Y.C.; Hsu, C.W.; Shih, S.J.; Chung, R.J. Angiogenesis, Osseointegration, and Antibacterial Applications of Polyelectrolyte Multilayer Coatings Incorporated With Silver/Strontium Containing Mesoporous Bioactive Glass on 316L Stainless Steel. Front. Bioeng. Biotechnol. 2022, 10, 1-14, doi: 10.3389/fbioe.2022.818137.

Daley, E.L.H.; Coleman, R.M.; Stegemann, J.P. Biomimetic microbeads containing a chondroitin sulfate/chitosan polyelectrolyte complex for cell-based cartilage therapy. J. Mater. Chem. B 2015, 3, 7920-7929, doi: 10.1039/C5TB00934K.

Peng, M.; Zhang, X.; Xiao, X.; Dong, M.; Zhao, G.; Liu, P.; Chen, Y.; Wang, C. Polyelectrolytes fabrication on magnesium alloy surface by layer-by-layer assembly technique with antiplatelet adhesion and antibacterial activities. J. Coatings Technol. Res. 2019, 16, 857-868, doi: 10.1007/s11998-018-00162-6.

Rodrigues, M.N.; Oliveira, M.B.; Costa, R.R.; Mano, J.F. Chitosan/Chondroitin Sulfate Membranes Produced by Polyelectrolyte Complexation for Cartilage Engineering. Biomacromolecules 2016, 17, 2178-2188, doi: 10.1021/acs.biomac.6b00399.

Varshosaz, J.; Sadeghi aliabadi, H.; Asheghali, F. Chondroitin/doxorubicin nanoparticulate polyelectrolyte complex for targeted delivery to HepG2 cells. IET Nanobiotechnology 2017, 11, 164-172, doi: 10.1049/iet-nbt.2015.0109.

Khan, A.R.; Yang, X.; Du, X.; Yang, H.; Liu, Y.; Khan, A.Q.; Zhai, G. Chondroitin sulfate derived theranostic and therapeutic nanocarriers for tumor-targeted drug delivery. Carbohydr. Polym. 2020, 233, 115837, doi:10.1016/j.carbpol.2020.115837.

Tabandeh, S.; Leon, L. Engineering Peptide-Based Polyelectrolyte Complexes with Increased Hydrophobicity. Molecules 2019, 24, 868, doi: 10.3390/molecules24050868.

Fajardo, A.R.; Lopes, L.C.; Pereira, A.G.B.; Rubira, A.F.; Muniz, E.C. Polyelectrolyte complexes based on pectin-NH2 and chondroitin sulfate. Carbohydr. Polym. 2012, 87, 1950-1955, doi:10.1016/j.carbpol.2011.09.096.

Werner, P.; Schuenke, P.; Krylova, O.; Nikolenko, H.; Taupitz, M.; Schröder, L. Investigating the Role of Sulfate Groups for the Binding of Gd3+ Ions to Glycosaminoglycans with NMR Relaxometry. ChemMedChem 2022, 202100764, doi: 10.1002/cmdc.202100764.

Varshosaz, J.; Asefi, H.; Hashemi-Beni, B.; Ghaffari, S.; Davoudi, A. Preparation and in vitro evaluation of novel cross-linked chondroitin sulphate nanoparticles by aluminium ions for encapsulation of green tea flavonoids. IET Nanobiotechnology 2018, 12, 757-763, doi: 10.1049/iet-nbt.2017.0298.

Suner, S.S.; Sahiner, M.; Ayyala, R.S.; Sahiner, N. Degradable and Non-Degradable Chondroitin Sulfate Particles with the Controlled Antibiotic Release for Bacterial Infections. Pharmaceutics 2022, 14, 1739, doi: 10.3390/pharmaceutics14081739.

Bourganis, V.; Karamanidou, T.; Kammona, O.; Kiparissides, C. Polyelectrolyte complexes as prospective carriers for the oral delivery of protein therapeutics. Eur. J. Pharm. Biopharm. 2017, 111, 44-60, doi: 10.1016/j.ejpb.2016.11.005.

Xue, W.; Liu, B.; Zhang, H.; Ryu, S.; Kuss, M.; Shukla, D.; Hu, G.; Shi, W.; Jiang, X.; Lei, Y.; et al. Controllable fabrication of alginate/poly-L-ornithine polyelectrolyte complex hydrogel networks as therapeutic drug and cell carriers. Acta Biomater. 2022, 138, 182-192, doi: 10.1016/j.actbio.2021.11.004.

Amoah, S.K.S.; Sandjo, L.P.; Kratz, J.M.; Biavatti, M.W. Rosmarinic Acid—Pharmaceutical and Clinical Aspects. Planta Med. 2016, 82, 388-406, doi: 10.1055/s-0035-1568274.

Demirci, S.; Sahiner, M.; Ari, B.; Sunol, A.K.; Sahiner, N. Chondroitin Sulfate-Based Cryogels for Biomedical Applications. Gels 2021, 7, 127, doi: 10.3390/gels7030127.

Suner, S.S.; Sahiner, M.; Mohapatra, S.; Ayyala, R.S.; Bhethanabotla, V.R.; Sahiner, N. Degradable poly(catechin) nanoparticles as a versatile therapeutic agent. Int. J. Polym. Mater. Polym. Biomater. 2022, 71, 1104-1115, doi: 10.1080/00914037.2021.1941957.

Panda, P.K.; Dash, P.; Yang, J.M.; Chang, Y.H. Development of chitosan, graphene oxide, and cerium oxide composite blended films: structural, physical, and functional properties. Cellulose 2022, 29, 2399-2411, doi: 10.1007/s10570-021-04348-x.

Panda, P.K.; Yang, J.M.; Chang, Y.H.; Su, W.W. Modification of different molecular weights of chitosan by p-Coumaric acid: Preparation, characterization and effect of molecular weight on its water solubility and antioxidant property. Int. J. Biol. Macromol. 2019, 136, 661-667, doi: 10.1016/j.ijbiomac.2019.06.082.

Hu, T.T.; Liu, F.; Dou, S.; Zhong, L. Bin; Cheng, X.; Shao, Z.D.; Zheng, Y.M. Selective adsorption of trace gaseous ammonia from air by a sulfonic acid-modified silica xerogel: Preparation, characterization and performance. Chem. Eng. J. 2022, 443, 136357, doi: 10.1016/j.cej.2022.136357.

Liu, J.; Li, X.; Lin, J.; Li, Y.; Wang, T.; Jiang, Q.; Chen, D. Sarcandra glabra (Caoshanhu) protects mesenchymal stem cells from oxidative stress: A bioevaluation and mechanistic chemistry. BMC Complement. Altern. Med. 2016, 16, 423, 1-11, doi: 10.1186/s12906-016-1383-7.

\* cited by examiner

REGULATED DRUG DELIVERY VIA CONTROLLED DEGRADABLE CHONDROITIN SULFATE PARTICLES

CROSS-REFERENCE TO RELATED APPLICATION

This application claims the benefit of U.S. Provisional Application 63/265,101, filed on Dec. 8, 2021, the contents of which are hereby incorporated in its entirety.

FIELD OF THE INVENTION

Disclosed herein are crosslinked chondroitin sulfate particles crosslinked chondroitin sulfate particle polyelectrolytes. The particles are useful in drug delivery applications. The particles may be used to treat various conditions, including bacterial and fungal infections.

BACKGROUND

Chondroitin sulfate (CS) is a non-immunogenic and non-toxic sulfated glycosaminoglycan (GAGs) comprising N-acetyl galactosamine and glucuronic acid found in proteoglycans in connective tissues. CS-derived materials have been used as wound dressing, tissue scaffold, coating materials, diagnostic devices, and biosensors. Chemically crosslinked polymeric particles from natural sources are considered as safe, effective, and stable crosslinked materials which swell in a suitable solvent and can carry various types of active agents to treat diverse diseases. Development of advanced polymeric carrier systems are of considerable interest in material design for clinical treatment because of significant advantages including safety, biocompatibility, biodegradability, less immunogenicity, as well as reducing the toxicity and side effects of the drugs, and enhancing the solubility of the drugs, controlling the release amount, and especially providing the long-term release kinetics and targeted delivery.

Biological polyelectrolytes (PECs), also called as biological polyelectrolyte complexes are generally comprised of strong intermolecular interactions known as Coulomb's interactions or electrostatic interactions between oppositely charged groups e.g., cationic compounds and biopolymers such as chitosan, poly-1-lysine, poly-L-arginine, insulin, collagen, amino dextran and 2-(diethylamino) ethyl dextran, with anionic biopolymers such as pectin, alginate, xanthan gum, dextran derivatives, hyaluronic acid, carrageenan, neem gum, heparin, chondroitin sulfate, carboxymethyl cellulose, humic substances, poly($\gamma$-glutamic acid), DNA, and siRNA. PECs assemblies have been used in wide range of applications as tissue adhesives and scaffolds for tissue engineering, hematostats, biosensors, implantable materials, template for enzyme immobilization, antimicrobial agents, and especially drug delivery devices. The interaction between the oppositely components of PECs also ensure high adherence to biological tissues thus renders mucoadhesive biological activity.

In the treatment of bacterial ulcers on the cornea such as *Pseudomonas* keratitis, the high ophthalmic toxicity and poor pharmacokinetics of the common drugs such as tobramycin and amikacin offer limited use in the clinical application due to the low drug permeability to the epithelial membrane necessitating frequent administration. Sustainable antibiotic delivery by means of natural biocompatible carbohydrate-based polymeric particles to establish prolonged antibiotic delivery at target sites e.g., into cornea offers vital infection treatment methods without the need for repeated administration of the toxic drug formulations (e.g., eye drops, ointments).

There remains a need for improved chondroitin sulfate particles. The remains a need for improved particles with enhanced safety, biocompatibility, biodegradability, and less immunogenicity. The remains a need for improved drug carriers for administration of therapeutics. The remains a need for systems and methods of reducing the innate toxicity and side effects associated with a given therapeutic agent. There remains a need for improved systems and methods for treating infective diseases, including bacterial infections, fungal infections, viral infections, and parasitic infections. There remains a need for improved systems and methods for the treatment of ophthalmologic diseases and conditions, especially infections in and around the eye. There remains a need for improved systems and methods for the treatment of bacterial ulcers, including ocular bacterial ulcers.

DETAILED DESCRIPTION

Figure 1:
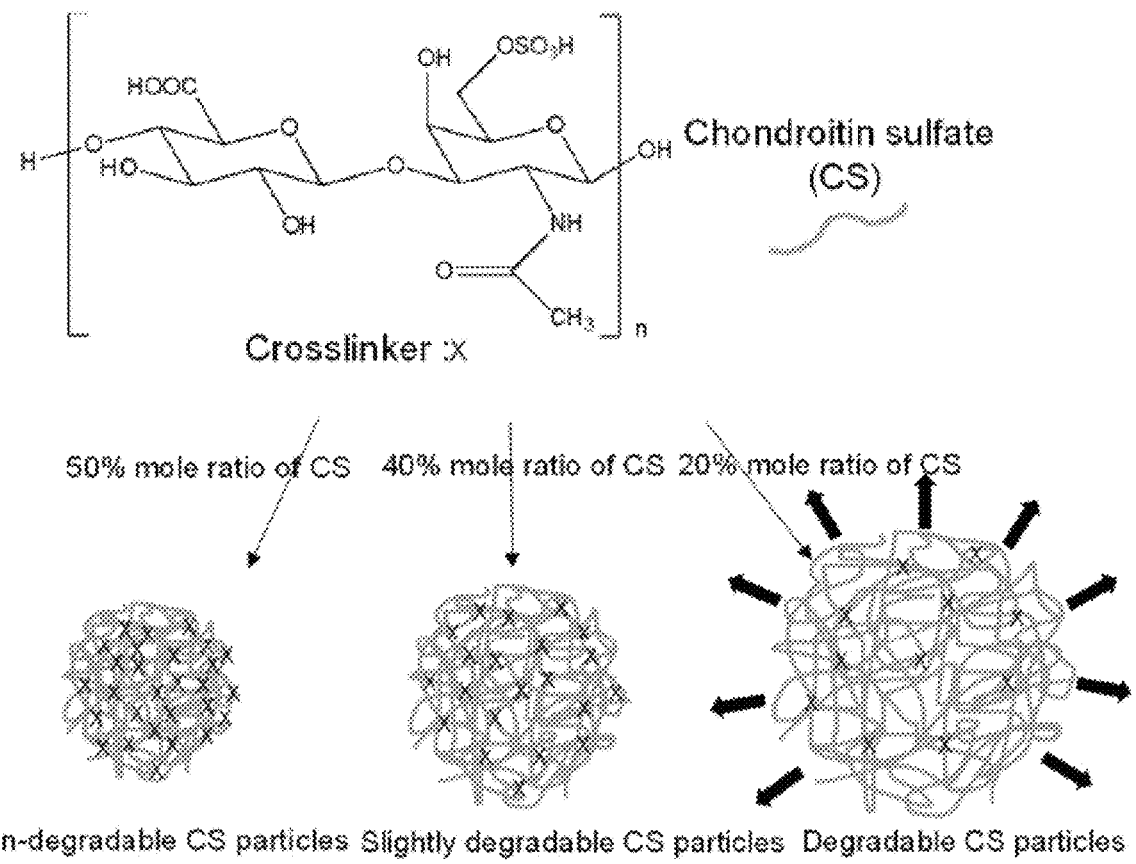
FIG. 1 depicts a schematic representation of non-degradable, slightly degradable, and completely degradable CS particles prepared using DVS crosslinker at 50, 40, and 20 mole % of CS repeating unit.
Figure 2:
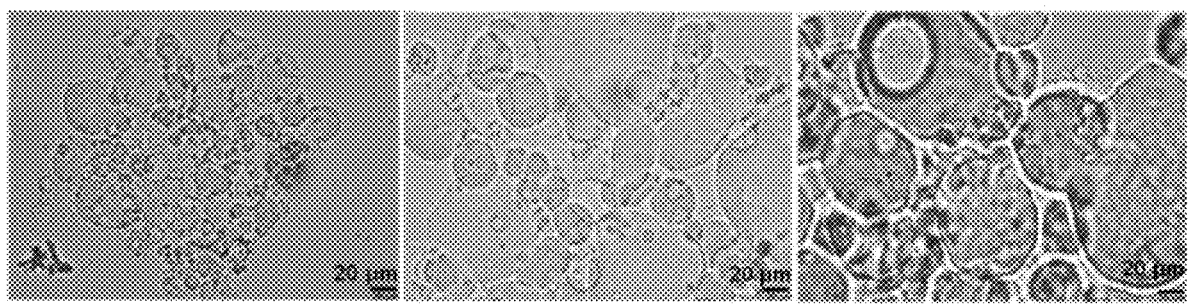
FIG. 2 depicts optical microscope images of non-degradable, slightly degradable, and completely degradable CS particles.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Compounds disclosed herein may be provided in the form of pharmaceutically acceptable salts. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate.

Disclosed herein are crosslinked chondroitin sulfate particles having at least one active agent encapsulated there within. Chondroitin sulfate is a naturally occurring glycosaminoglycan composed of a repeating disaccharide having the formula:

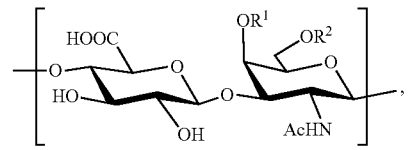

wherein one of $R^1$ or $R^2$ is $OSO_3Na$ and the other is H. Chondroitin sulfate is often provided as the sodium salt. Chondroitin Sulfate A is the compound defined when $R^1$ is $OSO_3Na$ and $R^2$ is H. Unless specified to the contrary, reference to "chondroitin sulfate" should be understood to mean chondroitin sulfate A. The chondroitin sulfate can be provided as the sodium salt, however, the skilled person understands that in the presence of appropriate media, the sodium cation may be exchanged either completely or partially with a different cation. Unless specified to the contrary, reference to chondroitin sulfate is not limited to any particular cationic counterion.

In certain implementations the crosslinked chondroitin sulfate particles can be characterized by the nature of the starting chondroitin sulfate polysaccharide prior to crosslinking. In certain implementations, the uncrosslinked chondroitin sulfate can have an average molecular weight from 5,000-500,000 Da, from 5,000-250,000 Da, from 5,000-100,000 Da, from 5,000-75,000 Da, from 5,000-50,000 Da, from 5,000-40,000 Da, from 5,000-30,000 Da, from 5,000-20,000 Da, from 5,000-10,000 Da, from 10,000-50,000 Da, from 10,000-40,000 Da, from 10,000-30,000 Da, from 10,000-20,000 Da, from 20,000-50,000 Da, from 20,000-40,000 Da, from 20,000-30,000 Da, from 30,000-50,000, or from 40,000-50,000. In certain implementations, the uncrosslinked chondroitin sulfate having the given average molecular weights is chondroitin sulfate, sodium salt.

In certain implementations, the uncrosslinked chondroitin sulfate can have a viscosity average molecular weight from 5,000-500,000 Da, from 5,000-250,000 Da, from 5,000-100,000 Da, from 5,000-75,000 Da, from 5,000-50,000 Da, from 5,000-40,000 Da, from 5,000-30,000 Da, from 5,000-20,000 Da, from 5,000-10,000 Da, from 10,000-50,000 Da, from 10,000-40,000 Da, from 10,000-30,000 Da, from 10,000-20,000 Da, from 20,000-50,000 Da, from 20,000-40,000 Da, from 20,000-30,000 Da, from 30,000-50,000, or from 40,000-50,000. In certain implementations, the uncrosslinked chondroitin sulfate having the given viscosity average molecular weights is chondroitin sulfate, sodium salt.

In some implementations the chondroitin is covalently crosslinked. In some implementations the chondroitin sulfate may first be functionalized with a moiety capable of underdoing a subsequent crosslinking reaction. Exemplary functionalizations include formation of (meth)acrylate esters with one or more of the hydroxyl groups present in the chondroitin sulfate. The (meth)acrylated chondroitin may then be crosslinked using radical-based techniques known in the art. In some implementations the chondroitin sulfate may be directly reacted with a crosslinking agent to provide the crosslinked particles. In some implementations, the crosslinker is one or more of divinyl sulfone ("DVS"), a bis-epoxide such as butanediol-diglycidyl ether ("BDDE"), 1,2,3,4-diepoxybutane, 1,2,7,8-diepoxyoctane, poly(ethylene glycol)diglycidyl ether, or a bis-carbodiimide like p-phenylene BDCI. In certain implementations, the chondroitin sulfate is crosslinked with DVS.

The crosslinked chondroitin sulfate particles may be characterized by the crosslink ratio. As used herein, "crosslinking ratio" refers to the molar ratio of the crosslinking agent relative to the number of disaccharide unit in the uncrosslinked chondroitin sulfate. In some implementations the crosslinked chondroitin sulfate particles can have a crosslinking ratio from 25-75%, from 25-50%, from 40-60%, from 50-75%, from 25-35%, from 30-40%, from 35-45%, from 40-50%, from 40-55%, from 45-55%, from 45-60%, from 50-60%, from 55-65%, from 60-70%, or from 65-75%.

The crosslinked chondroitin sulfate particles may be characterized by their particle size (measured as described herein). In some implementations, the crosslinked chondroitin sulfate particles have an average particle size from 100-10,000 nm, from 100-1,000 nm, from 500-2,500 nm, from 1,000-5,000 nm, from 2,500-7,500 nm, from 5,000-10,000 nm, from 100-500 nm, from 250-750 nm, from 500-1,000 nm, from 500-1,500 nm, from 500-2,000 nm, or from 1,000-2,500 nm.

The crosslinked chondroitin sulfate particles may be characterized by their zeta potential. In some implementations, the crosslinked chondroitin sulfate particles have a zeta potential from 1-60 mV, from 1-5 mV, from 5-25 mV, from 10-50 mV, from 10-30 mV, from 10-20 mV, from 20-50 mV, from 20-40 mV, from 30-40 mV, from 30-50 mV, or from 30-40 mV.

The crosslinked chondroitin sulfate particles may be characterized by their polydispersity. In some implementations, the crosslinked chondroitin sulfate particles have a polydispersity from 0.05-0.8, from 0.1-0.8, from 0.1-0.7, from 0.1-0.6, from 0.1-0.5, from 0.1-04, from 0.1-0.3 from 0.1-0.3, from 0.2-0.5, from 0.3-0.5, or from 0.4-0.7.

The crosslinked chondroitin sulfate particles may be in the form of a polyelectrolyte. As used herein, a crosslinked chondroitin sulfate particles polyelectrolyte refers to a particle in which some or all of the carboxylic acid groups in the chondroitin sulfate are ionically paired with a nitrogenous cation. In some embodiments, the nitrogenous cation is ammonium ($NH_4±$). In other embodiments, the nitrogenous cation is an alkyl amine, an amino acid, a polyamine, a peptide, or an aminocarbohydrate. Exemplary alkyl amines include monoalkyl amines, dialkyl amines, and trialkyl amines, wherein the alkyl groups are $C_{1-8}$ alkyl groups, optionally substituted one or more times by an aromatic ring. As used herein, amino acids refer to α-amino acids, β-amino acids, γ-amino acids and the like. Exemplary amino acids include the twenty-two canonical amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, esters thereof, as well an unnatural amino acids, oligopeptides composed of such amino acids. Unless specified to the contrary, reference to α-amino acids refers to the L enantiomer, the D enantiomer, and mixtures thereof. In certain embodiments, the α-amino acid is the L enantiomer. In some embodiments, the nitrogenous cation is a peptide, for example insulin, collagen, gelatin, and the like. In some implementations, the nitrogenous cation is a polyamine, 8hile88e poly-lysine, poly-arginine, polyethylenimine, and the like. In some implementations, the nitrogenous cation is an aminocarbohydrate, for example glucosamine, chitosan, aminodextran, and the like. In some implementations, at least 50%, at least 60%, at least 70%, at least 75%, at least 80%, at least 85%, at least 90%, or at least 95% of all the cationic counterions in the crosslinked chondroitin sulfate particles are nitrogenous cations.

The crosslinked chondroitin sulfate particles can have one or more active agents encapsulated therein. In some implementations, the active agent can include analgesic agents, anti-anxiety agents, anti-arthritic agents, antibiotic agents, anticancer agents, anticholinergic agents, anticonvulsants, antidepressants, antidiabetic agents, antidiarrheal agents, anti-emetic agents, antihistamines, antihyperlipidemic agents, antifungal agents, anti-inflammatory agents, antimigraine agents, anti-obesity agents, anti-oxidants, antipruritic agents, antipsychotic agents, antispasmodic agents, antiviral agents, aracidal agents, contraceptive agents, diuretic agents, hormones, anti-hormones, immunosuppressive agents, leukotriene inhibitors, narcotic agonists, narcotic antagonists, neurotransmitters, nucleic acids, peptide drugs, thrombolytic agents, vasodilators, or a combination thereof.

In certain implementations, the active agent is present in an amount from 10-5,000 μg active agent per 1 mg crosslinked chondroitin sulfate. When the crosslinked chondroitin sulfate particles include more than one active agent, the given mass refers to the total mass of the combined active agents. In some implementations, the active agent is present in an amount from 10-1,000 μg/mg, from 1,000-2,000 μg/mg, from 2,000-3,000 μg/mg, from 3,000-4,000 μg/mg, from 4,000-5,000 µg/mg, from 10-100 µg/mg, from 10-500 µg/mg, from 10-250 µg/mg, from 50-1000 µg/mg, from 50-250 µg/mg, from 100-250 µg/mg, from 100-500 µg/mg, from 100-300 µg/mg, or from 200-500 µg/mg.

In some implementations, the crosslinked chondroitin sulfate particles can include one or more anti-infectives. As used herein, an "anti-infective" is an agent intended to treat or prevent infection with an exogenous pathogen. In some implementations, the anti-infective can be an antibiotic, an antifungal, an aracidal (anti-parasitic), an anti-viral, or a combination thereof.

In some implementations, the crosslinked chondroitin particles include one or more antibiotics. In certain implementations, the crosslinked chondroitin particles include one or more penicillins, cephalosporins, quinolones (including fluoroquinolones), aminoglycosides, monobactams, carbapenems, tetracyclines, macrolides, peptides, and combinations thereof. In some embodiments, the antibiotics is one or more compounds selected from streptomycin, neomycin, kanamycin, amikacin, gentamycin, tobramycin, sisomicin, arbekacin, apramycin, netilmicin, paromomycin, spectinomycin, ciprofloxacin, levofloxacin, lomefloxacin, moxifloxacin, norfloxacin, ofloxacin, sparfloxacin, trovafloxacin, gatifloxacin, 10hile101010e10hi, cinoxacin, nalidixic acid, azithromycin, clarithromycin, dirithromycin, erythromycin, roxithromycin, troleandomycin, telithromycin, spectinomycin, indolicidin, defensin, cecropin, magainin, vancomycin, teicoplanin, telavancin, ramoplanin, decaplanin, bleomycin, colistin (polymyxin E), colistin A (polymyxin E1), colistin B (polymyxin E2), colistin sulfate, colistimethate sodium, actinomycin, bacitracin, polymyxin B, gentamicin, gentamicin sulfate, neomycin, kanamycin, tobramycin, metronidazole, clotrimazole, secnidazole, ornidazole, tinidazole, linezolid, doxycycline, tetracycline, oxytetracycline, chlortetracycline, demeclocycline, lymecycline, meclocycline, methacycline, minocycline, rolitetracycline, and tigecycline.

In certain implementations, the antibiotic is present in an amount from 10-5,000 antibiotic per 1 mg crosslinked chondroitin sulfate. When the crosslinked chondroitin sulfate particles include more than one antibiotic agent, the given mass refers to the total mass of the combined antibiotics. In some implementations, the antibiotic is present in an amount from 10-1,000 µg/mg, from 1,000-2,000 µg/mg, from 2,000-3,000 µg/mg, from 3,000-4,000 µg/mg, from 4,000-5,000 µg/mg, from 10-100 µg/mg, from 10-500 µg/mg, from 10-250 µg/mg, from 50-1000 µg/mg, from 50-250 µg/mg, from 100-250 µg/mg, from 100-500 µg/mg, from 100-300 µg/mg, or from 200-500 µg/mg.

In some implementations, the crosslinked chondroitin particles include one or more antifungals. In certain implementations, the crosslinked chondroitin particles include one or more polyene antifungals, imidazole antifungals, triazole antifungals, triazole antifungals, allylamine antifungals, sordarin, flucytosine, or echinocandin antifungals. In some implementations, the crosslinked chondroitin particles include one or more polyene antifungals, Exemplary polyene antifungals include amphotericin B, candicidin, filipin, hamycin, natamycin and rimocidin. In some implementations, the crosslinked chondroitin particles include one or more imidazole antifungals. Exemplary imidazole antifungals include bifonazole, butoconazole, clotrimazole, econazole, fenticonazole, isoconazole, ketoconazole, luliconazole, miconazole, omoconazole, oxiconazole, sertaconazole, sulconazole, and tioconazole. In some implementations, the crosslinked chondroitin particles include one or more triazole antifungals. Exemplary triazole antifungals include albaconazole, fluconazole, isavuconazole, itraconazole, 10hile101010e10hi, ravuconazole, terconazole, and voriconazole. In some embodiments, the thiazole antifungal is abafungin. In certain embodiments, the crosslinked chondroitin particles include an allylamine antifungal such as 11hile111111e11, butenafine, naftifine, and terbinafine. In some embodiments, the echinocandin antifungal is one or more of anidulafungin and micafungin.

In certain implementations, the antifungal is present in an amount from 10-5,000 µg active agent per 1 mg crosslinked chondroitin sulfate. When the crosslinked chondroitin sulfate particles include more than one antifungal, the given mass refers to the total mass of the combined antifungal agents. In some implementations, the antifungal is present in an amount from 10-1,000 µg/mg, from 1,000-2,000 µg/mg, from 2,000-3,000 µg/mg, from 3,000-4,000 µg/mg, from 4,000-5,000 µg/mg, from 10-100 µg/mg, from 10-500 µg/mg, from 10-250 µg/mg, from 50-1000 µg/mg, from 50-250 µg/mg, from 100-250 µg/mg, from 100-500 µg/mg, from 100-300 µg/mg, or from 200-500 µg/mg.

In some implementations, the crosslinked chondroitin particles include one or more antivirals. In certain implementations, the crosslinked chondroitin particles include one or more rotease inhibitors, endonuclease inhibitors, integrase inhibitors, enzyme inhibitors, non-nucleoside reverse transcriptase inhibitors, fusion inhibitors, cell entry inhibitors, mRNA and protein synthesis inhibitors cannabinoids, viral replication blockers, uncoating inhibitors, reverse transcriptase inhibitors, topoisomerase inhibitors, assembly inhibitors, M2 inhibitors, DNA polymerase inhibitors, DNA terminase complex inhibitors, HCV protein inhibitors, and neuraminidase inhibitors.

In some implementations, the crosslinked chondroitin particles include one or more protease inhibitors, for example amprenavir (or the pro-drug fosamprenavir), atazanavir, bepridil, boceprevir, darunavir, ebastine, indinavir, lopinavir, nelfinavir, ritonavir, rupintrivir, saquinavir, simeprevir, telaprevir, and tipranavir. In some implementations, the crosslinked chondroitin particles include one or more nucleoside reverse transcriptase inhibitors, for example abacavir, lamivudine, stavudine, didanosine, zidovudine, emtricitabine, zalcitabine, and tenofovir. In some implementations, the crosslinked chondroitin particles include one or more non-nucleoside reverse transcriptase inhibitors, for example doravirine, efavirenz, etravirine, loviride, and rilpivirine.

In certain implementations, the antiviral is present in an amount from 10-5,000 µg active agent per 1 mg crosslinked chondroitin sulfate. When the crosslinked chondroitin sulfate particles include more than one antiviral, the given mass refers to the total mass of the combined antiviral agents. In some implementations, the antiviral is present in an amount from 10-1,000 µg/mg, from 1,000-2,000 µg/mg, from 2,000-3,000 µg/mg, from 3,000-4,000 µg/mg, from 4,000-5,000 µg/mg, from 10-100 µg/mg, from 10-500 µg/mg, from 10-250 µg/mg, from 50-1000 µg/mg, from 50-250 µg/mg, from 100-250 µg/mg, from 100-500 µg/mg, from 100-300 µg/mg, or from 200-500 µg/mg.

In certain embodiments, the crosslinked chondroitin sulfate particles include an aracidal agent. Suitable aracidal agents include ivermectin, permethrin, niclosamide, tea tree oil, benzoyl peroxide, tapinarof, metronidazole, tea tree oil, and combinations thereof.

In some implementations, the active agent includes one or more analgesics. Suitable analgesics include opioids, capsaicin, diclofenac, lidocaine, benzocaine, methyl salicylate, trolamine, prilocaine, pramoxine, dibucaine, phenol, tetracaine, camphor, dyclonine, and menthol.

In certain embodiments, the crosslinked chondroitin sulfate particles include one or more anti-inflammatory agents. Suitable anti-inflammatories include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, and zomepirac sodium.

In some implementations, the active agent includes one or more steroids, for example clobetasol, betamethasone, diflorasone, fluocinonide, flurandrenolide, halobetasole, amcinonide, desoximetasone, halcinonide, fluticasone, triamcinolone, fluocinolone, hydrocortisone, dexamethasone, difluprednate, fluoromethalone, loteprednol etabonate, rimexolone mometasone, triamcinolone, alclometasone, denoside, prednicarbate, and combinations thereof.

In certain implementations, the active agent can be a progestogen such as 21-acetoxypregnenolone; allylestrenol; anagestone (17α-hydroxy-6α-methylpregn-4-en-20-one); anagestone 17α-acetate; chlormadinone; chlormadinone 17α-acetate; chloroethynyl norgestrel; cyproterone; cyproterone 17α-acetate; desogestrel; dienogest; dimethisterone (6α,21-dimethylethisterone); drospirenone (1,2-dihydrospirorenone); ethisterone (17α-ethinyltestosterone or pregneninolone); ethynerone; etynodiol diacetate (norethindrol diacetate); etonogestrel (11-methylene-levo-norgestrel; 3-keto-desogestrel); gestodene; hydroxyprogesterone (17α-hydroxyprogesterone); hydroxyprogesterone caproate; hydroxyprogesterone acetate; hydroxyprogesterone heptanoate; levonorgestrel; lynestrenol; medrogestone (6,17α-dimethyl-6-dehydroprogesterone); medroxyprogesterone; medroxyprogesterone acetate; megestrol; megestrol acetate; segesterone acetate; nomegestrol; nomegestrol acetate; norethindrone (norethisterone; 19-nor-17α-ethynyltestosterone); norelgestromin (17-deacetylnorgestimate); noretynodrel; norgestrienone; progesterone; and retroprogesterone.

In some instances, the active agent can be an estrogenic compound. Suitable estrogenic compounds include estradiol, estradiol esters, including estradiol benzoate, valerate, cypionate, heptanoate, decanoate, acetate and diacetate; 17α-estradiol; ethinylestradiol, ethinylestradiol esters (e.g., ethinylestradiol 3-acetate and ethinylestradiol 3-benzoate); estriol; estriol succinate; polyestrol phosphate; estrone, estrone esters (e.g., estrone acetate, estrone sulfate, and piperazine estrone sulfate); quinestrol; mestranol; conjugated equine estrogens, and combinations thereof.

In some implementations, the active agent includes a CNS therapeutic agent, for instance an anti-psychotic such as paliperiodone, risperidone, lurasidone, lloperidone, ziprasidone, aripiprazole, brexipiprazole, caripazine, asenapine, clozapine, olanzapine, quetiapine, zotepine, blonanserin, pimavanserin, sertindole, phenothiazines, thioxanthenes, butyrophenones such as benpridol, bromperidol, droperidol, haloperidol, and timiperone. The active agent can be a cholinesterase inhibitor such as physostigmine, neostigmine, pyridostigmine, ambenonium, demecarium, rivastigmine, galantamine, and donepezil. Other suitable CNS agents include memantine and ergot alkaloids.

In some implementations, the active agent includes one or more antioxidants. In some implementations, the antioxidant is a natural antioxidant (i.e., a compound or mixture of compounds that is produced by a plant, animal, or other organism). In some implementation the antioxidant is a phenol (which can be a polyphenol), a carotenoid, an anthocyanin, a chlorophyl, a flavonoid, or a combination thereof. In some implementations, the antioxidant is vitamin A or beta-carotene, pantothenic acid, panthenol, niacinamide, asiaticoside, madecassoside, 14hile1414 acid, madecassic acid, ascorbic acid, dehydroascorbic acid, vitamin E, vitamin K, 14hile141414e14hins, epigallocatechin, epigallocatechin-3-gallate, fucoxanthin, resveratrol, rosmarinic acid, eupatorine, ginsenoside, sulforaphane, bisdemethoxycurcumin, axifolin, hesperidin, cyanidin, catechin, demethoxycurcumin, curcumin, genistein, plastoquinones, sargaquinoic acid, sargachromenol, aloe vera, quercetin, kaempferol, myricetin, rutin, diosmetin, diosmin, or a combination thereof. In some implementations, the antioxidant is provided as part of a plant extract. Exemplary plant extracts that may be used include *Corallina pilulifera* extract, algae extract, *Ecklonia cava* extract, extracts derived from green tea, rosemary, grape seed, basil grape, blueberry, tomato, acerola seed, pine bark, milk thistle, and combinations thereof.

In certain implementations, the antioxidant is present in an amount from 10-5,000 µg active agent per 1 mg crosslinked chondroitin sulfate. When the crosslinked chondroitin sulfate particles include more than one antioxidant, the given mass refers to the total mass of the combined antioxidant agents. In some implementations, the antioxidant is present in an amount from 10-1,000 µg/mg, from 1,000-2,000 µg/mg, from 2,000-3,000 µg/mg, from 3,000-4,000 µg/mg, from 4,000-5,000 µg/mg, from 10-100 µg/mg, from 10-500 µg/mg, from 10-250 µg/mg, from 50-1000 µg/mg, from 50-250 µg/mg, from 100-250 µg/mg, from 100-500 µg/mg, from 100-300 µg/mg, or from 200-500 µg/mg.

In other embodiments, the active agent includes one or more veterinary drugs, for instance aracidals, antiprotozoals, antibiotics, insecticides, anthelmintics, antifungals, anti-inflammatories, antirheumatics, steroids, and combination thereof.

In some implementations the crosslinked chondroitin sulfate particles (and polyelectrolytes) provide controlled release of therapeutics. The crosslinked chondroitin sulfate particles (and polyelectrolytes) provide reduced toxicity compared to delivery of the drugs separate from the particles. The controlled release permits one time dosing of a formulation, whereas prior formulations may require multiple dosing events with decreased convenience to the subject.

The crosslinked chondroitin sulfate particles (and polyelectrolytes) may be formulated in a wide variety of pharmaceutical compositions for instance those including pharmaceutically acceptable carriers. Suitable carriers include water, saline and other liquid formulations, which can be directly administered to a desired location in or on a subject. In other cases, the particles can be included in a formulation for topical administration, for instance, lotions, sprays, creams, ointments and the like. The compositions can also include a backing layer to secure the composition at an application site.

The pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

Dosage forms for topical and/or transdermal administration of the particles may include ointments, pastes, creams, lotions, gels, powders, solutions, suspensions, sprays, inhalants and/or patches. Generally, the active component is admixed under sterile conditions with a pharmaceutically acceptable excipient and/or any needed preservatives and/or buffers as may be required. Unless specified to the contrary, topical administration includes administration to one or more locations on, within, or around the eye. Additionally, the present invention contemplates the use of transdermal patches. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically administrable formulations may, for example, comprise from about 1% to about 99% (w/w) of the crosslinked chondroitin sulfate particles. In some implementations, the concentration of the crosslinked chondroitin sulfate particles (which includes the mass of the particle and any encapsulated active agent) is from 1-5%, 1-10% (w/w), 5-15% (w/w), 10-20% (w/w), 15-25% (w/w), 25-50% (w/w), 50-75% (w/w), or 75-99% (w/w). Formulations for topical administration may further comprise one or more of the excipients and/or additional ingredients described herein.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxy ethylene sorbitan [Tween 60], polyoxy ethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

The compositions can also include on or more moisturizing agents, i.e., a substance that adds or restores moisture to the skin. Representative examples of moisturizing agents that are usable in the present invention include, without limitation, acetamide monoethanolamine urazole, aloe vera in any of its variety of forms (e.g., aloe vera gel), allantoin, guanidine, glycolic acid and glycolate salts (e.g. ammonium salt and quaternary alkyl ammonium salt), hyaluronic acid, lactamide monoethanolamine, polyethylene glycols, polyhydroxy alcohols (e.g., sorbitol, glycerol, hexanetriol, propylene glycol, butylene glycol, hexylene glycol and the like), sugars and starches, sugar and starch derivatives (e.g., alkoxylated glucose), and any combination thereof.

The compositions can also include one or more penetration enhancers, i.e., a compound that improves the bioavailability of a topically delivered agent. Representative penetration enhancers include, for example, and without limitation, such agents as 1-substituted azacycloheptane-2-ones (e.g., 1-n-dodecylcyclazacycloheptan-2-one, available under the trademark Azone® from Whitby Research Incorporated, Richmond, Va.), dipolar-aprotic solvents (e.g., N,N-dimethylacetamide ("DMA"), decylmethylsulfoxide ("C10 MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

The compositions may include antioxidants, chelating agents, antimicrobial preservatives, antifungal preservatives, alcohol preservatives, acidic preservatives, and the like. In some implementations, when listed in the context of an excipient, the listed ingredients are not encapsulated in the crosslinked chondroitin sulfate particles. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and perfuming agents. In certain embodiments for parenteral administration, conjugates can be mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U. S. P. and isotonic sodium chloride solution, etc. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Compositions suitable for topical delivery on, within, or around the eye can be formulated as a solution or liquid dispersions, and can include water as a carrier. In some embodiments, the compositions can include water in an amount from 25.0-99.9 wt %, from 50.0-99.9 wt %, from 75.0-99.9 wt %, from 95.0-99.9 wt %, from 80.0-99.0 wt %, from 85.0-99.0 wt %, 90.0-98.0 wt %, from 85-95 wt %, from 75.0-90.0 wt %, from 65.0-80.0 wt %, from 55.0-70 wt %, from 45.0-60.0 wt %, from 35.0-50.0 wt %, or from 25.0-45.0 wt %.

The compositions may be formulated at a pH suitable for administration to one or more locations on, within, or around the eye. In certain embodiments, the composition has a pH from 4.0-8.0, from 5.0-8.0, from 6.0-8.0, from 6.0-7.5, from 6.0-7.0, from 6.0-6.5, from 6.5-7.0, from 6.5-7.5, from 6.5-8.0, from 7.0-7.5, from 7.0-8.0, from 7.5-8.0, from 7.1-7.5, from 7.2-7.5, or from 7.3-7.5.

The compositions may be formulated with a tonicity suitable for administration to one or more locations on, within, or around the eye, for example, the composition can be isotonic to lacrimal fluid. In other embodiments, the composition can be hypertonic to lacrimal fluid. The composition can have an osmolarity from 250-500 mOsm/L, from 250-450 mOsm/L, from 250-400 mOsm/L, from 250-350 mOsm/L, from 250-325 mOsm/L, from 280-325 mOsm/L, or from 300-325 mOsm/L.

The compositions may be formulated at a viscosity suitable for administration to one or more locations on, within, or around the eye. Viscosity may be measured at 23° C., at a shear rate of 1 Hz. Suitable viscosities for the compositions include 1-10,000 cps, 1-5,000 cps, 2,500-10,000 cps, 2,500-7,500 cps, 5,000-10,000 cps, 1-100 cps, 25-250 cps, 25-100 cps, 50-150 cps, 50-250 cps, 100-500 cps, 250-750 cps, 500-1,000 cps, 500-1,500 cps, 1,000-2,000 cps, 1,500-2,500 cps, 2,000-3,000 cps, 2,500-3,500 cps, 3,000-4,000 cps, 3,500-4,500 cps, 4,000-5,000 cps, 4,500-5,500 cps, 5,000-6,000 cps, 5,500-6,500 cps, 6,000-7,000 cps, 6,500-7,500 cps, 7,000-8,000 cps, 7,500-8,500 cps, or 9,000-10,000 cps.

The composition may be formulated as an ocular ointment. Exemplary ointments will include a pharmaceutically acceptable base, for example liquid petrolatum, white petrolatum, plastibase, hard paraffin, white soft paraffin, yellow soft paraffin, liquid paraffin, emulsifying wax, microcrystalline wax, white bees wax, yellow bees wax, carnauba wax, wool wax (wool fat), mineral oil, olive oil, purified lanolin, anhydrous lanolin, polyethylene glycol (e.g., polyethylene glycol 400 or polyethylene glycol 3350), propylene glycol, polyoxyethylene, polyoxypropylene, and combinations thereof. In other embodiments, the composition does not include a base, as defined herein.

The composition may be formulated as ocular emulsion having an oil phase, which can include one or more emulsifiers, emollients, or combination thereof. Suitable emulsions can include an oil phase in an amount from 15-75 wt %, from 15-50 wt %, from 15-30 wt %, from 20-40 wt %, from 25-50 wt %, from 30-60 wt %, or from 45-75 wt %. The composition can include an emulsifier in an amount from 1-20 wt %, from 1-10 wt %, from 5-15 wt %, or from 10-20 wt %.

In certain embodiments, the ocular compositions disclosed can include vegetable oil, mineral oil, animal oil, synthetic oil, silicone oils, isopropyl palmitate, 1-decene polymer (hydrogenated), C12-C15 alkyl benzoate, C12-C15 alkyl benzoates esters, lanolin alcohol, isopropyl myristate, or a combination thereof.

In certain embodiments, the ocular compositions can include a surfactant, for example an ionic surfactant, nonionic surfactant, or a combination thereof. Exemplary surfactants include cetostearyl alcohol, cetyl alcohol, cocamide DEA, cocamide MEA, isoceteth-20, oleyl alcohol, sorbitan monostearate, sorbitan tristearate, stearyl alcohol, tyloxapol, softigen, solutol HS15, poloxamers (e.g., Pluronic F-68LF™, Lutrol F68, Pluronic L-62LF™, Pluronic L62D™ polysorbates (e.g., polysorbate 20 and polysorbate 80), polyoxyethylene fatty acid esters (e.g., Emulphor) and combination thereof. In other embodiments, the composition does not include a surfactant.

In certain embodiments, the ocular compositions can include a gelling agent. In some embodiments, the composition can include gum, agar, carrageenan, petrolatum, carboxymethylcellulose, hydroxyethyl cellulose, hydroxymethyl cellulose, sodium hyaluronate, or a combination thereof. In other embodiments, the composition does not include a gelling agent.

Suitable excipients for the formulation can include petrolatum, mineral oil, sodium hyaluronate, propylparaben, methylparaben, polysorbate, dimethicone, cyclomethicone, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, carboxymethylcellulose, polycarbophil, sodium alginate, lanolin oil, carbomer homopolymer type b (allyl pentaerythritol crosslinked), or benzalkonium chloride. However, in some embodiments, the composition does not include a paraben.

In some implementations, the crosslinked chondroitin sulfate particles (and crosslinked chondroitin sulfate particle polyelectrolytes) can be used to treat infections. Exemplary infections include bacterial infections, fungal infections, viral infections, and/or parasitic infections. In certain implementations, the compositions can be used to treat ophthalmologic infections, for instance those caused by *Aspergillus, Staphylococcus, Streptococcus, Peptostreptococcus, Corynebacterium, Clostridium, Listeria, Bacillus, Enterobacteriaceae, Pseudomonas, Moraxella, Helicobacter, Stenotrophomonas, Bdellovibrio, Legionella, Candida, Trychophyton*, or combination thereof. In certain implementations, the compositions can be used to treat infections cause by *Staphylococcus aureus*, Methicillin-resistant *Staphylococcus aureus* (MRSA), *Pseudomonas aeruginosa, Escherichia coli, Candida albicans, Aspergillus niger, Trichophyton rubrum, S. pneumoniae, H. influenza*, and *S. pyogenes*.

In some implementations, the compositions may be used to treat bacterial keratitis. In some implementations, the method is a method of treating bacterial ulcers on the cornea, for example due to *Pseudomonas* keratitis In some implementations, the crosslinked chondroitin sulfate particles (and crosslinked chondroitin sulfate particle polyelectrolytes) may be used in the treatment of wounds. As used herein, the term "wound" refers to physical disruption of the continuity or integrity of tissue structure. Wounds may be acute or chronic and include cuts and lacerations, surgical incisions or wounds, punctures, grazes, scratches, compression wounds, abrasions, friction wounds, decubitus ulcers (e.g. pressure or bed sores); thermal effect wounds (burns from cold and heat sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g., psoriasis and eczema, stomach or intestinal ulcers, oral wounds, including a ulcers of the mouth, damaged cartilage or bone, amputation wounds and corneal lesions.

As used herein, the term "chronic wound" refers to a wound that has not healed within a normal time period for healing in an otherwise healthy subject. Chronic wounds may be those that do not heal because of the health of the subject, for example, where the subject has poor circulation or a disease such as diabetes, or where the subject is on a medication that inhibits the normal healing process. Healing may also be impaired by the presence of infection, such as a bacterial, fungal or parasitic infection. In some instances, a chronic wound may remain unhealed for weeks, months or even years. Examples of chronic wounds include but are not limited to, diabetic ulcers, pressure sores and tropical ulcers (i.e., jungle rot).

In some implementations, the crosslinked chondroitin sulfate particles can be used for treating or preventing inflammation.

In some embodiments, topical compositions containing the crosslinked chondroitin sulfate particles can be used for treating or preventing a skin, as well as for promoting healthy skin in a subject.

In some embodiments, topical compositions containing the crosslinked chondroitin sulfate particles can be used in the treatment of inflammation, such as skin inflammation. In certain embodiments, the topical compositions containing the crosslinked chondroitin sulfate particles can be used in the treatment of diseases that may benefit from inhibition of infiltration and activation of inflammatory cells (e.g. neutrophils, lymphocytes, monocytes, mast cells), and/or inhibition of expression and activation of cell surface adhesion molecules (e.g. VCAM-1 and ICAM-1) in endothelial and inflammatory cells. In some implemenations, the topical compositions containing the crosslinked chondroitin sulfate particles can be used to treat inflammation (acute or chronic), inflammation associated with spinal cord injury to promote nerve regeneration, inhibition of rejection of transplanted cells and tissues, inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), neurodegenerative disorders (e.g., Parkinson's disease, Alzheimer's disease, Huntington's disease, Dementia pugilistica, Pick's disease, Guam parkinsonism dementia complex, Fronto-temporal dementia, Cortico-basal degeneration, Pallido-pontal-nigral degeneration, Progressive supranuclear palsy, Dementia with Lewy bodies (DLB), and multiple system atrophy (MSA)).

In certain implementation the crosslinked chondroitin sulfate particles may be used in various cosmetic contexts. In some implementations, the crosslinked chondroitin sulfate particles, optionally encapsulated with one or more antioxidants or cosmetic active agent, may be used to increase the firmness of skin, reduce and/or prevent wrinkles, minimize or reduce scarring, and increasing the elasticity of skin.

In certain implementation the crosslinked chondroitin sulfate particles may be used to treat a skin condition, disease, or disorder. In some implementations, the crosslinked chondroitin sulfate particles, optionally encapsulated with one or more antioxidants or cosmetic active agent, may be used to treat candidiasis, impetigo, psoriasis, eczema, acne or dermatitis.

The crosslinked chondroitin sulfate particles may be prepared by combining uncrosslinked chondroitin sulfate with one or more crosslinking in the desired molar ratio. In some implementations, an inverse emulsion is used at the reaction medium.

In certain implementations the crosslinked chondroitin sulfate particles are combined with a crosslinker in an inverse emulsion that includes an aqueous phase, a hydrophobic phase, and one or more surfactants. The aqueous phase may be an alkaline solution. Suitable alkaline solutions include 0.1-1.0 M NaOH, 0.1-0.5 M NaOH, 0.1-0.25 M NaOH, 0.25-1.0 M NaOH, or 0.5-1.0 M NaOH. In some implementations the sodium hydroxide may be replaced with a different base, e.g., potassium hydroxide and the like. An organic co-solvent may be included in the aqueous phase, for instance a water soluble organic solvent like methanol, ethanol, isopropanol, acetone, DMSO, and the like. When present the organic co-solvent may be in a concentration of 1-25% (vol/vol). The hydrophobic phase may be an oil, such as described above, or may be a hydrocarbon solvent such as a $C_{6-12}$ hydrocarbon. In some implementations the hydrophonic phase includes heptane, octane, decane, isooctane, or a combination thereof.

In certain implementations, the surfactant is one or more water-soluble surfactants. In some implementations the surfactant is one or more anionic water-soluble surfactants. In some implementations, the surfactant is one or more of sodium alkyl diphenyl ether disulfonate, sodium polyoxyethylene alkyl ether sulfate, sodium polyoxyethylene aryl ether sulfate, sodium alkyl sulfate, sodium alkyl benzene sulfonate, ammonium lauryl sulfate, potassium lauryl sulfate, sodium myreth sulfate, and dialkyl sodium sulfosuccinate. In certain embodiments, the surfactant is sodium or potassium oleate, triethanolamine stearate, sodium lauryl sulfate, sodium dioctyl sulfosuccinate, and sodium docusate.

The uncrosslinked chondroitin sulfate may be combined with the aqueous phase at concentration from 1-1,000 mg/mL, from 1-500 mg/mL, from 1-250 mg/mL, from 1-1,000 mg/mL, from 5-50 mg/mL, from 10-100 mg/mL, from 10-50 mg/mL, from 50-100 mg/mL, or from 100-250 mg/mL. One or more active agents may be included in the aqueous phase at a desired concentration.

The resulting mixture may be combined with the hydrophobic phase and surfactant and mixed to produce inverse emulsion. The crosslinker may then be added to the inverse emulsion with continuous mixing, either as a neat reagent or in a suitable solvent. One or more active agents may be included in the crosslinked solution. After mixing for sufficient time, the crosslinked chondroitin sulfate may be separated from the reaction mixture, for instance by precipitation via addition of an anti-solvent.

To obtain crosslinked chondroitin sulfate polyelectrolyte the crosslinked particles may be combined with a nitrogenous base in a suitable solvent and mixed for a time sufficient for cation exchange. The crosslinked chondroitin sulfate polyelectrolyte may be separated from the solvent and unexchanged cations using known techniques.

EXAMPLES

The following examples are for the purpose of illustration of the invention only and are not intended to limit the scope of the present invention in any manner whatsoever.

Example 1: Preparation of Crosslinked Chondroitin Sulfate Particles

Chondroitin sulfate A sodium salt (CS, ≥98%, Average MW 10,000-30,000, Biosynth carbosynth, Compton, UK), divinyl sulfone (DVS, 97%, Merck, Darmstadt, Germany), dioctyl sulfosuccinate sodium salt (AOT, 96%, Acros Organics, Geel, Belgium), 2,4-trimethylpentane (isooctane, ≥99.5%, Isolab, Eschau, Germany), and acetone (99%, BRK, Istanbul, Turkey) were used for synthesis of CS particles and were used as received. Tobramycin (from local vender, Deva Holding, Istanbul, Turkey) and amikacin hydrate (≥96.5%, Sigma Aldrich, Saint Louis, MO, USA) antibiotics and trichloroacetic acid (99%, Carlo Erba, France) were purchased and used as received. Nutrient agar (NA, Condolab, Madrid, Spain) and nutrient broth (NB, Merck, Darmstadt, Germany) were used as bacterial growth medium and *Pseudomonas aeruginosa* ATCC 10145 (KWIK-STIK, Microbiologics, St. Cloud, MN, USA) gram-negative bacteria was used as received. The L929 fibroblast cells (Mouse C3/An connective tissue) were obtained from the SAP Institute, Ankara, Turkey. Trypsin (0.25%, EDTA 0.02% in PBS), Dulbecco's Modified Eagle's Medium (DMEM, with 4.5 g/L glucose, 3.7 g/L sodium pyruvate, L-Glutamine 0.5 g/mL), fetal bovine serum (FBS, heat inactivated), and penicillin/streptomycin (10,000 U/mL penicillin, 10 mg/mL streptomycin) were purchased from Panbiotech, Aidenbach, Germany. Dimethyl sulfoxide (DMSO, 99.9%, Carlo Erba, France) and 3-(4,5-dimethyl-thiazol-2-yl)-2,5-diphenyltetrazolium bromide (MTT agent, 98%, neofroxx, Einhausen, Germany) were purchased and used as received. Ultra-pure deionized water with resistivity of 18.2 M·Ω·cm was obtained from a Millipore Direct-Q 3 UV water purification system (Merck Darmstadt, Germany) and used for the preparation of all aqueous solutions.

The viscosity average molecular weight (Mv) of CS was determined by using Ubbelohde viscosimeter at room temperature. Briefly, 10 mg/mL concentration of CS solution was prepared in 0.2 M NaCl. Then, the intrinsic viscosity (dL/g) of the CS solution was evaluated by using the equation:

$$\eta_{red} = (t-t_0)/t_{0c} = (\eta-\eta_0)/\eta_{0c}$$

where $\eta_{red}$, $\eta$ and $\eta_0$ are the reduced viscosity and intrinsic viscosity of CS solution and the viscosity of the solvent, respectively, and t and $t_0$ are the flow time of the CS solution and solvent, respectively.

The $M_v$ of CS was determined by the using Mark-Houwink-Sakurada equation as the following equation:

$$[\eta] = K(M_v)^\alpha$$

The parameters of K and α are the constant value for CS-solvent combination at a certain temperature and these values were accepted as $K=5 \times 10^{-5}$ mL/g and α=1.1. $M_v$ is the viscosity average MW of CS and the value was determined as about $20 \times 10^3$ Da.

Chondroitin sulfate, sodium salt (0.3 g) was dissolved in 10 mL of 0.2 M NaOH solution, and 1 mL of this solution was dispersed in 30 mL 0.2 M AOT/isooctane solution to obtain inverse microemulsion under vigorous stirring at 1000 rpm. Mixing continued under the same conditions for 1 h to obtain a clear CS solution in the inverse micelles. Next, the crosslinker, DVS at 50, 40, and 20 mol % relative to the CS repeating unit, was added to the emulsion media under continuous vortex for dispersion and mixing continued at 1000 rpm for 1 h more at room temperature. The CS particles were precipitated in an excess amount of acetone. Then, the particles were washed with acetone three times by centrifugation at 10,000 rpm for 10 min to remove unreacted chemicals and surfactants. The obtained CS particles were dried with a heat gun and kept in a closed container for further use.

Optical light microscope (Olympus, BX53, Tokyo, Japan) and scanning electron microscope (SEM, SU70, Hitachi, Japan) were used to visualize the shape and size of the CS particles. For SEM analysis, dry CS particles were covered with palladium/gold to a few μm under a vacuum for 10 seconds. The elemental composition of CS particles was determined with an Energy Dispersive Spectrometry (EDS) detector attached to SEM (SU70, Hitachi, Japan). For size distribution analysis, CS-based particles were suspended in DI water at 1 mg/mL concentration and the hydrodynamic average diameter of the CS-based particles were measured by dynamic light scattering (DLS, 90 plus, Brookhaven Instrument Corp., Holtsville, N.Y., USA) with 35 mW solid state laser detector at an operating wavelength of 658 nm. The average values are given with standard deviations. Fourier Transform Infrared (FT-IR) spectra of CS-based materials was recorded in the frequency range of 4000 to 650 cm$^{-1}$ with 4 cm$^{-1}$ resolutions by using a FT-IR spectrophotometer (Perkin-Elmer, Spectrum 100, 100 Akron, Ohio, USA).

Degradation capability of CS particles prepared at three crosslinker ratios of 50, 40, and 20 mol % relative to the CS repeating unit was investigated under physiologic conditions in 0.01 M PBS at pH 7.4 and 37° C. In short, 30 mg of CS particles were suspended in 10 mL of PBS. These suspensions were placed in a water bath adjusted to 37° C. under 300 rpm mixing rate for certain times of 24 h, 48 h, 72 h, and 240 h. Then, the amount of CS particles in the PBS was precipitated by using a centrifuge at 10,000 rpm for 10 minutes and dried at 50° C. in an oven. The gravimetric degradation was evaluated as weight loss % of CS particles by the equation:

$$\text{Weight loss \%} = (M_0 - M_t)/M_0 \times 100$$

where $M_0$ gives the weight of the CS particles initially and $M_t$ shows the weight of the CS particles at time t, which was 24 h, 48 h, 72 h, and 240 h.

Figure 4:
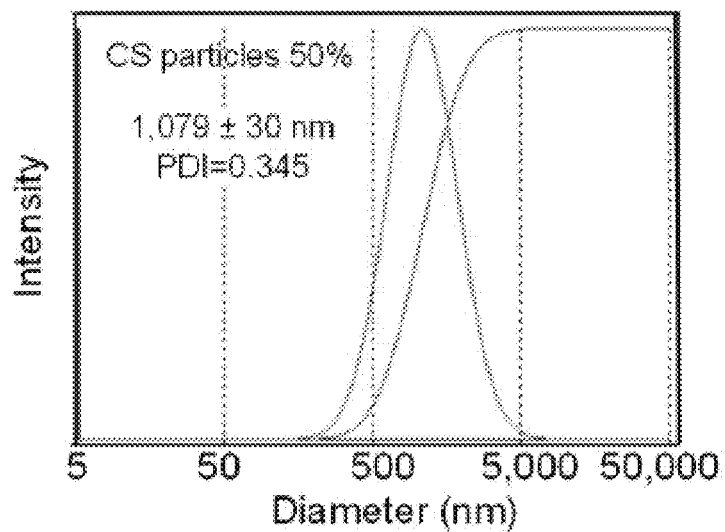
FIG. 4 depicts the hydrodynamic size distribution of CS particles crosslinked at 50% mole ratio.
Figure 5A:
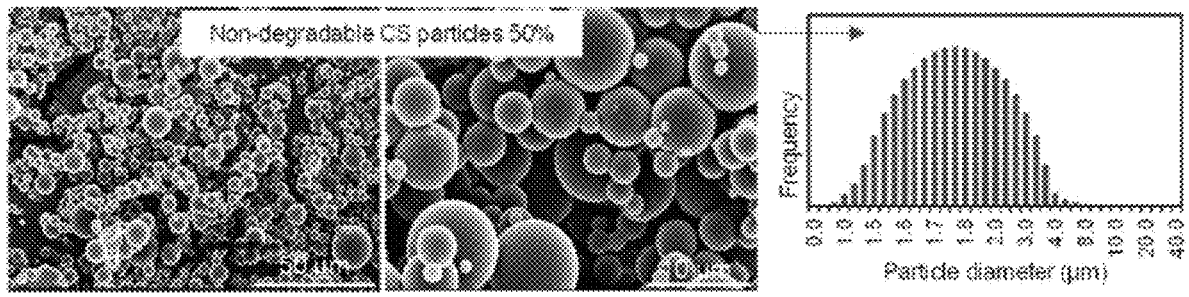
FIG. 5A depicts SEM images and size distribution of CS particles crosslinked at 50%.
Figure 5B:
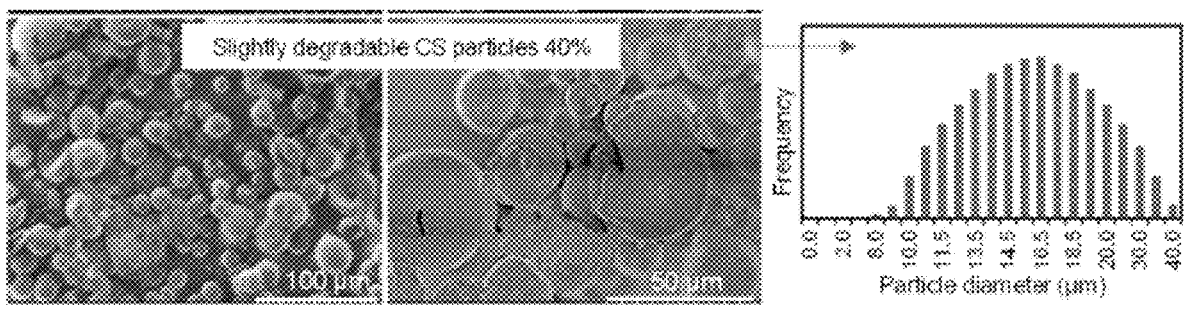
FIG. 5B depicts SEM images and size distribution of CS particles crosslinked at 40%.
Figure 6:
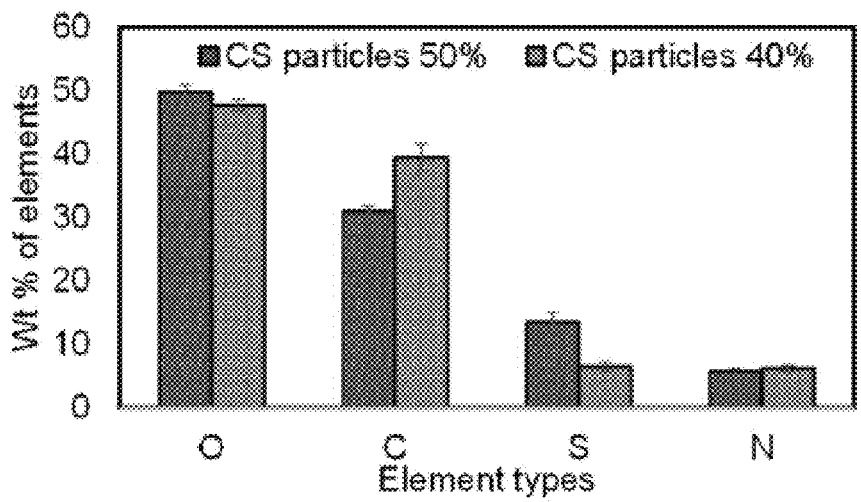
FIG. 6 depicts compositional analysis of CS particles crosslinked at 50% and 40%.

No degradation was obtained for CS particles at 50% up to 72 h and they were slightly degraded with 7.0±2.8% weight loss amount at 240 h. The optical microscope images of 50% CS particles supported these degradation results. The non-degradable CS particles crosslinked at 50% mole ratio are more stable within 72 h and some large size particles were degraded after 240 h. The 40% CS particles had slow degradation from 7.5±2.1% to 52.5±3.5% between 24 h and 240 h. The optical microscope images of CS particles at 40% demonstrated some degradation up to 48 h, but more than half of micron-sized CS particles were degraded at 240 h. The 40% CS particles are slightly degradable material in comparison to non-degradable 50% CS particles. Furthermore, CS particles were quickly degraded almost totally within 48 h with low crosslinker ratio in 20% CS particles. Thus, the degradability of CS particles can be controlled by regulating the crosslinker ratio in the particle network. Lower crosslinker ratio triggered the higher swelling ability of the particles. The hydrodynamic size distribution of CS particles was given with DLS measurements as presented in FIG. 4. The average size distribution of non-degradable 50% CS particles was measured as 1079±30 nm with 0.5-5 μm size range.

The dry CS particles, crosslinked at 50% had a smooth surface, distinct morphology with spherical shapes in the range of 0.5 to 5 μm. The dry form of CS particles crosslinked at 40% has almost spherical shapes with fragmented particle structures in the 5-40 μm size range. The surface structure of the dry CS particles crosslinked with a 20% mole ratio is rough with almost spherical shapes with particle sizes ranging from 5 to 50 μm. The size distribution range for 50% cross-linked CS particles were found to decrease almost ten-fold and five-fold with respect to 40% and 20% crosslinked CS particles, respectively. The sulfur content of the CS particles at 50% and 40% was found as 13.5% and 6.5% owing to the SEM-EDS analysis, but in theory, these values could be 12.3% and 11.7%, respectively. The higher sulfur content came from the presence of more DVS crosslinker in the particle network of 50% CS particles.

Figure 7:
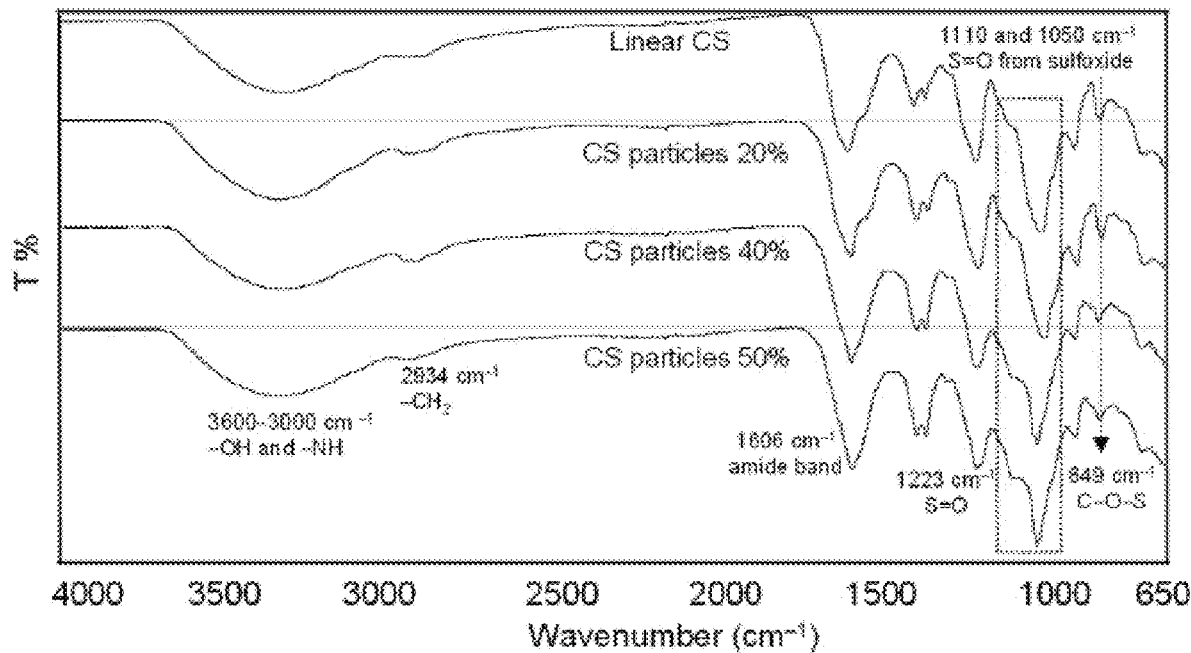
FIG. 7 depicts FT-IR spectra of linear CS and crosslinked CS particle (20%, 40%, and 50%).

FIG. 7 shows the FT-IR spectra for linear CS and its particle that are crosslinked at three ratios; 50%, 40%, and 20%. The spectra of CS particles at all crosslinker ratios were observed to contain the specific bands of linear CS as reported by a previous study. Briefly, the broad band from 3600 cm$^{-1}$ to 3000 cm$^{-1}$ related to OH and NH stretching, CH$_2$ stretching at 2934 cm$^{-1}$, amide I band at 1606 cm$^{-1}$, carbon-hydrogen vibrations at 1408 and 1375 cm$^{-1}$, S=O stretching at 1223 cm$^{-1}$, carbon-carbon vibration at 1040 cm-1, and C—O—S stretching at 849 cm$^{-1}$ were determined for all CS particles coming from the linear CS chains in the particle network. The CS particles crosslinked at 20-50% mole ratio had similar vibrational bands. The broad and strong peak at 1040 cm$^{-1}$ in the spectra of CS and low crosslinked CS turn into sharp peaks at 1050 cm$^{-1}$ with particle formation as can be seen in spectrum of highly crosslinked CS particles. The shoulder peak at 1110 cm$^{-1}$ and this sharp peak at 1050 cm$^{-1}$ attributed to presence of S=O stretching vibrations from sulfoxide groups of the crosslinker, DVS. The width of the peak at 1050 cm$^{-1}$ was significantly decreased with the increase in the ratio of crosslinker (DVS) for CS particles and while the peak intensity at 1110 cm$^{-1}$ was increased with the increase in the ration of the crosslinker. These results indicated that the crosslinker content of CS particles was increased by changing the DVS ratios from 20% to 50%.

Polyelectrolyte CS$^-$[NH$_4$]$^+$ microgels were attained by cation exchange reaction through ammonium hydroxide treatment of CS microgels. Shortly, 0.2 g of CS microgels were suspended in 50 mL of 6.25% aqueous ammonia solution and stirred at 200 rpm for an hour. The polyelectrolyte CS$^-$[NH$_4$]$^+$ microgels were precipitated by centrifugation at 10,000 rpm for 10 min and washed with acetone:water (50:50, v:v) mixture and then acetone. The obtained CS$^-$[NH$_4$]$^+$ microgels were dried with heat gun and kept for further use.

The swelling ability of CS microgels and CS$^-$[NH$_4$]$^+$ microgels at different pH range between 2 and 11 were analyzed by dynamic light scattering (DLS, Brookhaven Nanobrook Omni, USA) measurements. In brief, 1 mg/mL concentration of CS-based microgels were suspended in 1 mM KNO$_3$ aqueous solution and filtered with 5 μm pore size syringe filter for hydrodynamic average size distribution analysis. Furthermore, zeta potential was determined using 40 mg CS-based microgels suspension in 40 mL of 1 mM KNO$_3$ solution, and the zeta potential was measured against pH using zeta potential measuring devices (Brookhaven Nanobrook Omni, USA). DLS and zeta potential analysis were repeated for ten times and the results were given with standard deviations. Fourier Transform Infrared (FT-IR) spectra of CS-based microgels was recorded in the frequency range of 4000 to 650 cm$^{-1}$ with 4 cm$^{-1}$ resolutions by using a FT-IR spectrophotometer (Perkin-Elmer, Spectrum 100, Akron, USA). Thermal gravimetric analysis (TGA, Seiko, SII TG/DTA 6300, Japan) of 5 mg CS-based microgels was examined from 50 to 700° C. temperature range at a heating rate of 10° C./min under 100 mL/min nitrogen flow rate.

The chemical structure of CS microgels and CS$^-$[NH$_4$]$^+$ microgels were investigated by FT-IR analysis. The broad peak was observed in the range of 3600-3000 cm$^{-1}$ due to the O—H and N—H stretching of CS chains. The small peak at 2901 cm$^{-1}$ was attributed to C—H stretching of CH$_2$ groups of CS. The sharp peak at 1602 cm$^{-1}$ was assigned to the presence of amide band in the CS structure. Also, the peak at 860 cm$^{-1}$ was corresponding to C—O—S groups of CS structure in the microgel network. Among these CS peaks, the characteristic peaks of DVS were obtained at 1223 and 1030 cm$^{-1}$ stretching vibrations belong to S=O groups to confirm of the crosslinker structure of CS microgels. The difference peaks of polyelectrolyte CS$^-$[NH$_4$]$^+$ microgels was determined at 3250 cm$^{-1}$ broad band and 1414 cm$^{-1}$ stretching vibration attributed to NH$_4$$^+$ groups into the polyelectrolyte structure.

Figure 3:
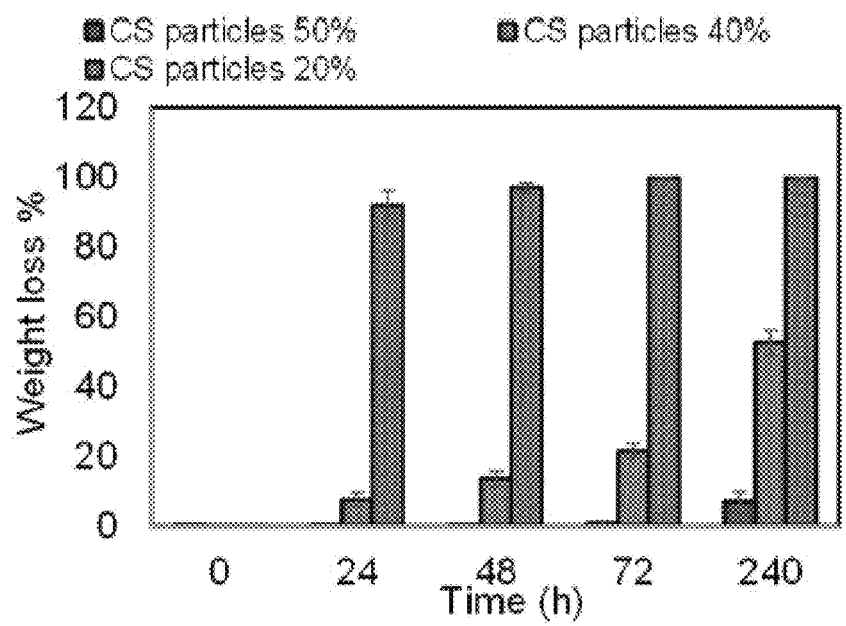
FIG. 3 depicts the weight loss % of CS particles prepared at 50, 40, and 20% crosslinked mole ratios. The particles were incubated for 24 h, 48 h, 72 h, and 240 h in physiological conditions at pH 7.4 and 37° C.

Thermal degradation of CS microgels and CS$^-$[NH$_4$]$^+$ microgels were acquired by thermogravimetric/differential thermogravimetric (TG/DTG) analysis (FIG. 3). The first slightly degradation shown in both thermogram at about 5.0% and 8.8% weight loss values at ~100° C. with slight DTG peaks were corresponding to the loss of bound water from the microgel structure of CS and CS$^-$[NH$_4$]$^+$ microgels, respectively. In addition, three main degradation steps occurred in the temperature ranges 214-260° C. with a maximum peak at 250° C. with 23.1% weight loss, at 260-400° C. range with a maximum peak at 318° C. with 39.4% weight losses, respectively and at 620-738° C. range with a maximum peak at 714° C. with 69.2% weight loss were observed for CS microgels. The thermogram of CS$^-$[NH$_4$]$^+$ microgels was shown three step degradations and the first degradation was detected at slightly low temperature range of 190-230° C. with a sharp DTG peak at 218° C. with 33.0% weight loss. More degradations were observed at the second degradation interval between 230-445° C. with two DTG peaks at ~282 and 422° C. with a total of 80.6% weight loss, and the third degradation step in 450-560° C. range with a maximum peak at 560° C. with 84.8% weight losses. The polyelectrolyte CS$^-$[NH$_4$]$^+$ microgels are thermally more degradable than CS microgels due to the presence of the ionic groups within the polymeric networks.

Figure 20:
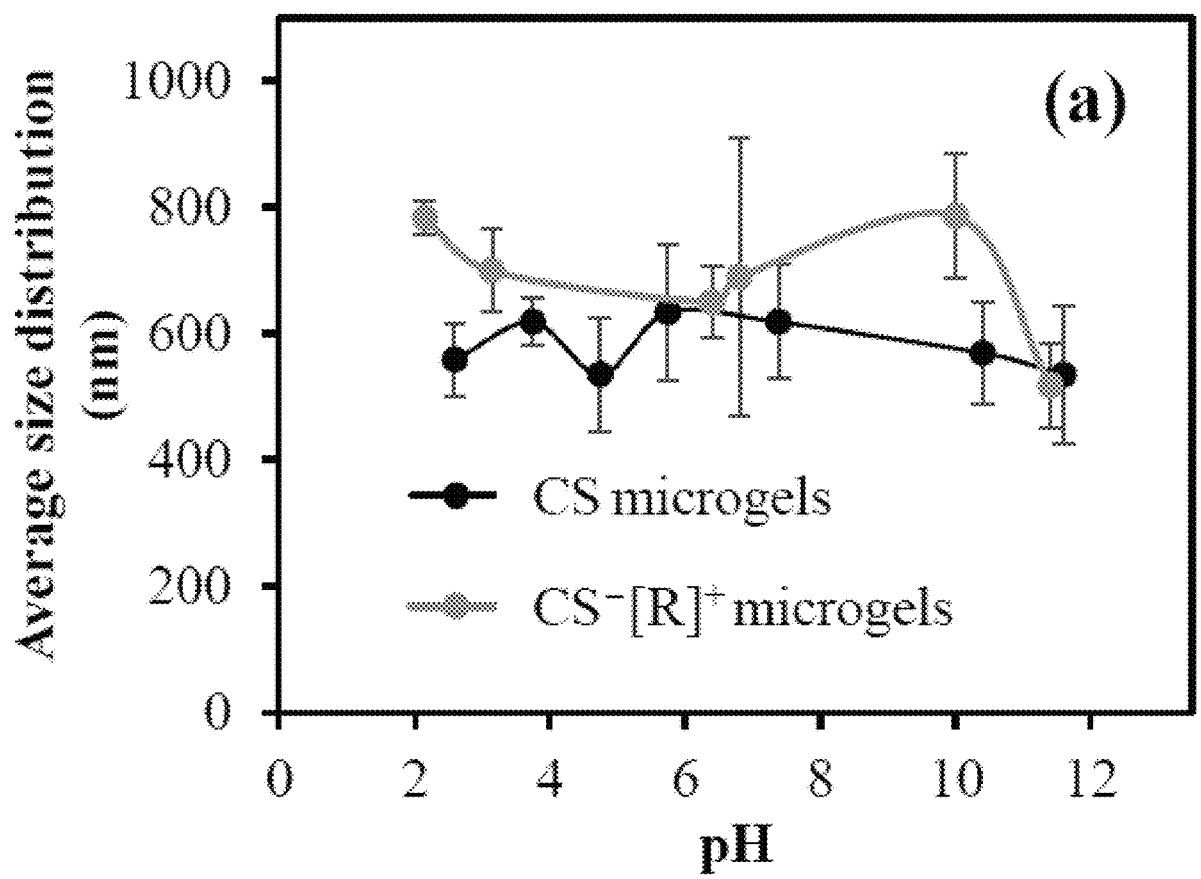
FIG. 20 depicts the size of CS microgels and $CS^-[R]^+$ microgels at different pH.

Polyelectrolyte complexes and their microgels are stimuli-responsive materials against the pH and ionic strength of the solvents and change their sizes and zeta potential values accordingly. Therefore, size measurements of CS microgels and CS$^-$[NH$_4$]$^+$ microgels at different solution pHs were carried out with DLS studies. The dimensions of CS microgels did not change much at different solution pH levels (FIG. 20). The microgel sizes were varied between 534 and 633 nm. The size of CS microgels were measured at 633±104 nm at 5.7 pH. The size of CS$^-$[NH$_4$]$^+$ microgels did not change significantly as highly crosslinked (50%) particles are used as the tighter network of CS chains are constructed the water swelling and ion-ion charge interactions were suppressed.

Figure 21:
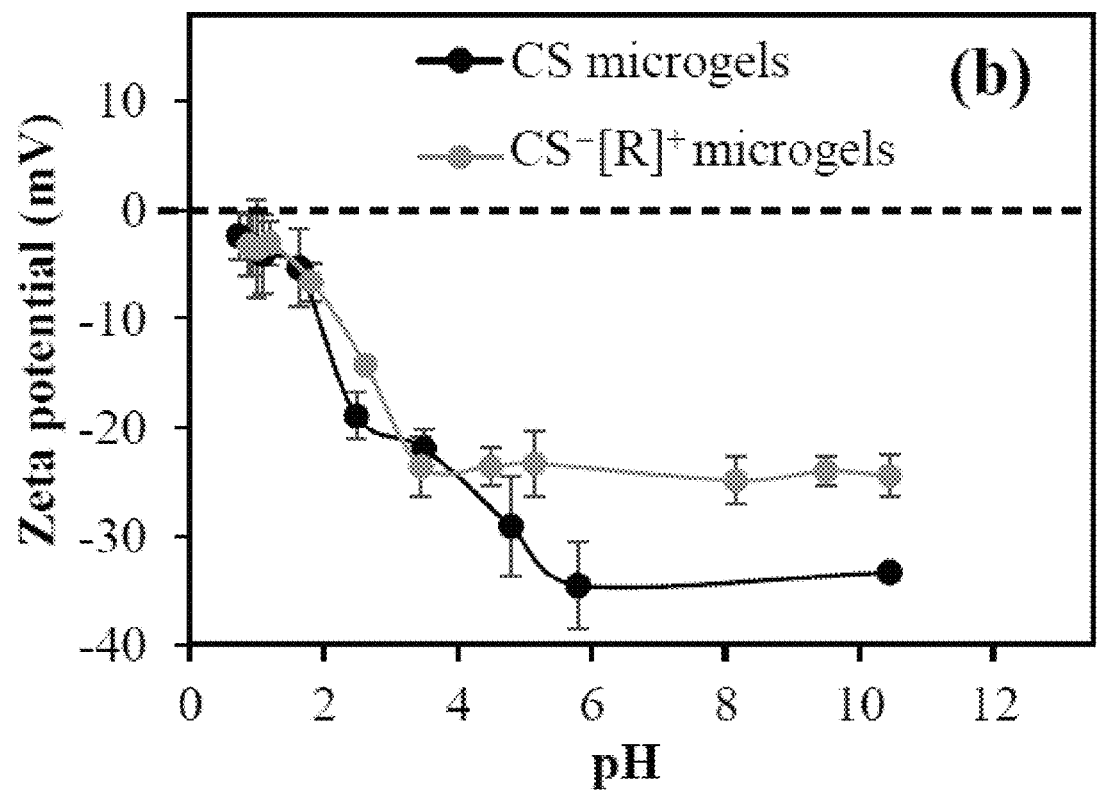
FIG. 21 depicts the pH versus zeta potential graphics of CS microgels and $CS^-[R]^+$ microgels in pH 1-10 range.

The zeta potentials of CS microgels and CS$^-$[NH$_4$]$^+$ microgels in 1 mM KNO$_3$ versus pH were measured. As presented in FIG. 21, the isoelectric point could not be detected in both microgels. The pH value was measured in 1 mM KNO$_3$ solution for CS microgel is 10.45 and the zeta potential at that pH value is −33.4±0.7 mV. For the CS$^-$[NH$_4$]$^+$ microgels, the measured pH is 8.5 and its zeta potential is −24.5±2.1 mV.

Example 2: Preparation of Drug Loaded Chondroitin Sulfate Particles

Antibiotic-loaded CS-Tobramycin and CS-Amikacin particles were prepared by encapsulation process using DVS crosslinker. In short, 30 mg/mL chondroitin sulfate ("CS") solution was prepared in 10 mL of 0.2 M NaOH solution. As a drug solution, 100 mg/mL concentration of Tobramycin or Amikacin drug was dissolved in 1 mL of DI water. These two solutions were mixed for 2 min. Then, 1.1 mL of the drug:CS solution was dispersed in 30 mL 0.2 M AOT/isooctane solution under vigorous stirring at 1000 rpm for 10 min. Then, the crosslinker DVS at 50, 40, and 20 mol % relative to the CS repeating unit, was added to the emulsion medium under continuous vortex for dispersion and mixing continued at 1000 rpm for 1 more h at room temperature. Next, the prepared CS-Tobramycin and CS-Amikacin particles were removed from the reaction medium and precipitated in excess acetone. Then, the particles were washed with acetone three times by centrifugation at 10,000 rpm for 10 min to remove unreacted chemicals and surfactant. Finally, the obtained drug-loaded CS-Tobramycin and CS-Amikacin particles were dried with a heat gun and kept in a closed container for further use.

Drug release from 20 mg CS-Tobramycin and CS-Amikacin particles were investigated by dispersing them in 1 mL of PBS at pH 7.4 and transferring this to a dialysis membrane (MW cut off 12kDA). The membrane containing the CS-Tobramycin/Amikacin particles was placed into 40 mL of PBS solution (pH 7.4) at 37° C. in a shaker bath. The amounts released into the PBS solution were evaluated by using high performance liquid chromatography (HPLC, Thermo Ultimate 3000, Germering, Germany) with a refractive index (RI) detector according to the previously proposed procedure for tobramycin and amikacin. Thermo Acclaim 120 C18 column (3 μm, 75 mm, 120 Å, reversed phase, Thermo Scientific, Sunnyvale, CA, USA) was used as a stationary phase at 30° C. column temperature. Mobile phase was prepared as 90:10 (methanol:water, v/v) mixture adjusted at pH 2 with trichloroacetic acid. The drug solutions were eluted isocratically in mobile phase with 1.0 mL/min flow rate for 10 min and retention times of tobramycin and amikacin drugs were determined at 4.1 and 3.5 min, respectively. The amount of released drug was calculated against the previously determined drug calibration curve in PBS at the same conditions. As the drug release was constant, the PBS solution was discarded, replenished with 40 mL of fresh PBS, and the release amount of drug was measured. The result is reported as cumulative release amounts. The experiments were repeated three times and presented with standard deviations.

Antibacterial activity of tobramycin and amikacin solutions and drug-loaded CS-Amikacin and CS-Tobramycin particles were investigated by using the disc diffusion method against *Pseudomonas aeruginosa* ATCC 10145. To determine the antibacterial activity of drugs as a control group, 20 μL of drug solutions at five different concentrations in physiologic serum, 50, 20, 10, 5, and 2 mg/mL, were treated with *P. aeruginosa* at different incubation times. Separately, 50 mg/mL concentration of drug-loaded CS particle suspension was prepared in physiologic serum and sterilized by UV irradiation for 2 min. Then, 0.1 mL of 107 CFU/mL bacteria suspension in nutrient broth was inoculated on the nutrient agar plates. Immediately, 9 mm sterile discs were placed on the center of the plate. Then, 50 μL of drug-loaded CS particle suspension was dropped on the sterile discs. Next, the plates were incubated at 37° C. for different incubation times. After the incubation, the inhibition zone (mm) was determined as the diameter of the clear zone.

In addition, minimum inhibition concentration (MIC) and minimum bactericidal concentration (MBC) values of the CS-Amikacin and CS-Tobramycin particles were also determined against *P. aeruginosa* by using microtiter broth dilution method. Briefly, 100 μL of nutrient broth as a liquid growth medium was placed into the each well on a 96-well plate and then 100 μl of 50 mg/mL concentration of drug-loaded CS particle suspension was added to the first well and diluted in a sequence by two-fold with the existing medium to prepare from 25 to 0.046 mg/mL concentrations. Then, 10 μL of 107 CFU/mL bacteria suspension in nutrient broth was added to the each well and the plate was incubated at 37° C. for 24 h. the lowest concentration of the drug-loaded CS particle with no visible growing depend on the transparency accepted as the MIC value. The medium for all the transparent wells was inoculated on nutrient agar as a solid medium and incubated at 37° C. for 24 h. The lowest concentration of the drug-loaded CS particle with no growing was accepted as MBC value.

*Pseudomonas aeruginosa* corneal ulcers can be severe compared with the other bacterial ulcers on the cornea. Tobramycin and amikacin are amino-glycoside antibiotics against a broad antibacterial spectrum, and are used as eye drops for the treatment of infections caused by *P. aeruginosa* because they have higher activity than other antibiotics such as gentamicin in suppressing *Pseudomonas* keratitis on the eye. Side effects such as tearing, swelling of the eye, itching, stinging, and burning of the eye, temporary blurred vision, and nephrotoxicity and ototoxicity limit the direct use of these drugs.

Furthermore, the high administration frequency of these drugs, every 1 hour, also makes them difficult to use. The prepared CS particles were utilized as drug carrying vehicle for tobramycin and amikacin antibiotics for the treatment of corneal *P. aeruginosa* ulcers. The encapsulation technique was used to load these antibiotics into the CS particle network because of multiple advantages that CS can render such as decreasing drug toxicity and side effects, enhancing loading and release capacity, prolonged release kinetics and so on. In the synthesis of crosslinked polymeric systems as a carrier material, drug molecules readily embedded inside the particles during the crosslinking reaction. The hydrodynamic size distribution and the polydispersity index values of bare and drug loaded CS particles crosslinked at 50% mole ratio were determined and provided in the table below:

| Drug carriers | Average size (nm) | Polydispersity Index (PDI) |
| --- | --- | --- |
| CS particles 50% | 1079 ± 30 | 0.345 |
| CS-Tobramycin particles 50% | 830 ± 25 | 0.270 |
| CS-Amikacin particles 50% | 776 ± 57 | 0.519 |

The average size of bare CS particles was slightly decreased upon drug loading for example, from 1079±30 nm to 830±25 nm for CS-Tobramycin particles and to 776±57 nm for CS-Amikacin particles. Drug release amount and release capacity of CS-Tobramycin and CS-Amikacin particles crosslinked at 50%, 40%, and 20% mole ratios are given in the table below:

| Drug carriers | Release amount (µg/mg) | Release capacity (%) |
| --- | --- | --- |
| CS-Tobramycin particles 50% | 200 ± 2 | 80 ± 0.8 |
| CS-Tobramycin particles 40% | 215 ± 8 | 86 ± 3.2 |
| CS-Tobramycin particles 20% | 192 ± 3 | 76 ± 1.2 |
| CS-Amikacin particles 50% | 228 ± 5 | 91 ± 2.0 |
| CS-Amikacin particles 40% | 242 ± 4 | 96 ± 1.6 |
| CS-Amikacin particles 20% | 214 ± 2 | 80 ± 0.8 |

Figure 8:
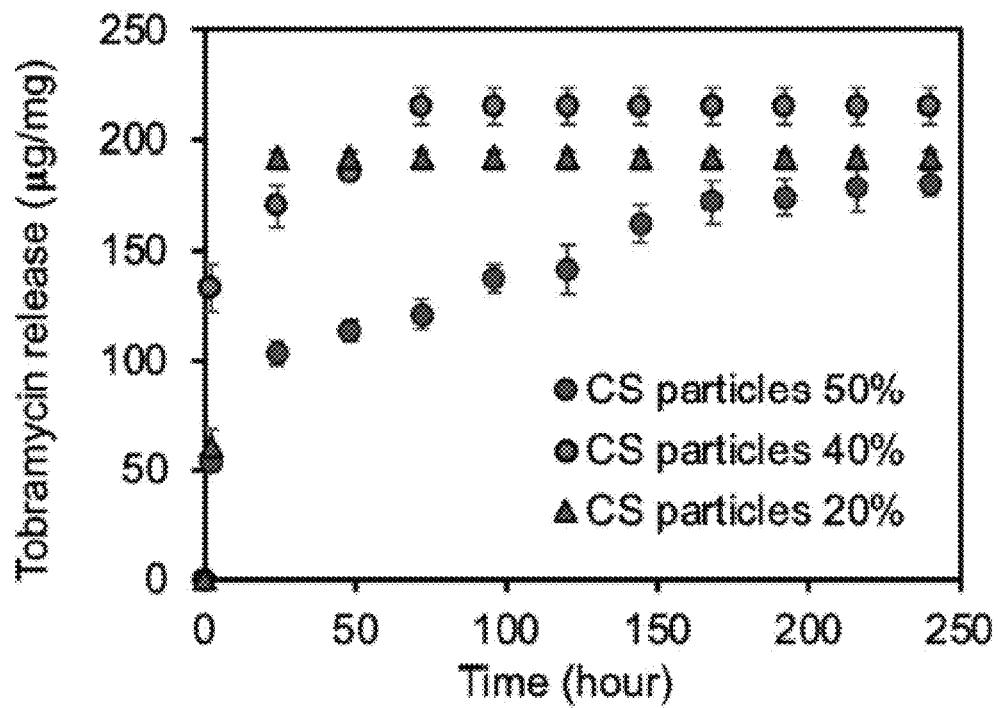
FIG. 8 depicts the drug release profiles of CS-Tobramycin particles crosslinked at 50, 40, and 20% mole ratios, measured in pH 7.4 PBS at 37.5° C.
Figure 9:
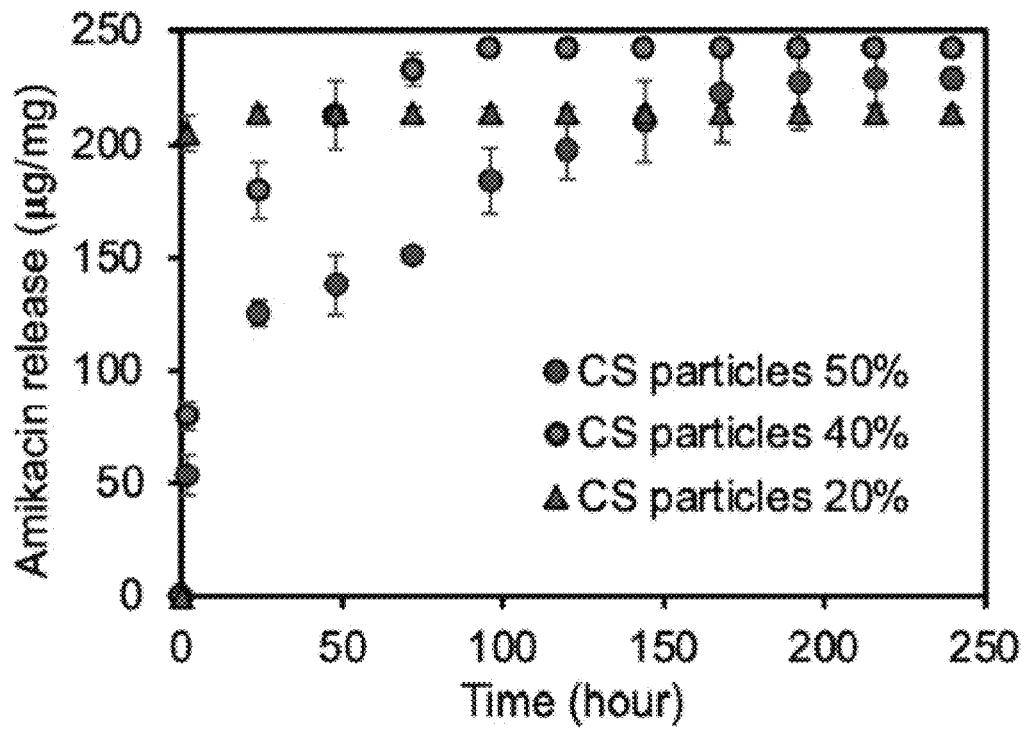
FIG. 9 depicts the drug release profiles of CS-Amikacin particles crosslinked at 50, 40, and 20% mole ratios, measured in pH 7.4 PBS at 37.5° C.
Figure 10:
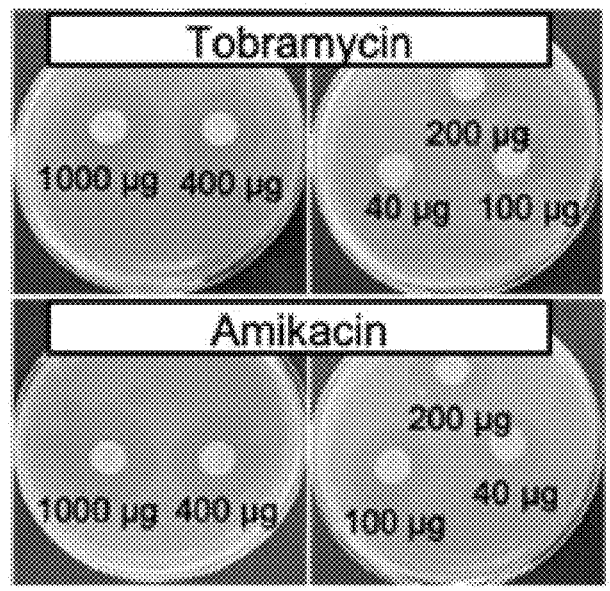
FIG. 10 depicts the inhibition zone (mm) for tobramycin and amikacin drugs at different concentrations; 20 µL of 2-50 mg/mL for 24 h incubation.
Figure 11:
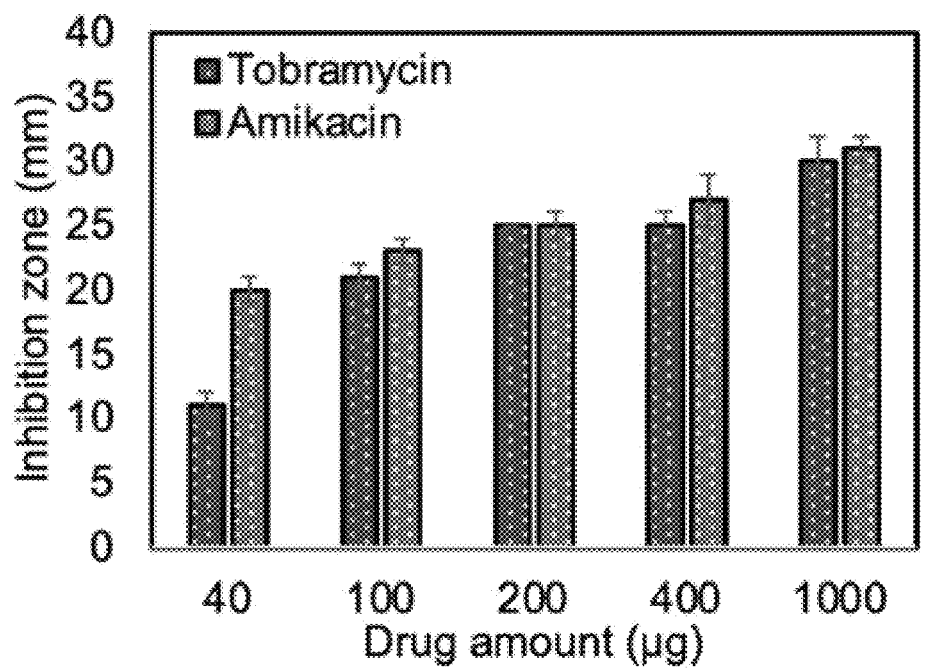
FIG. 11 depicts an analysis of the images in FIG. 10.
Figure 12:
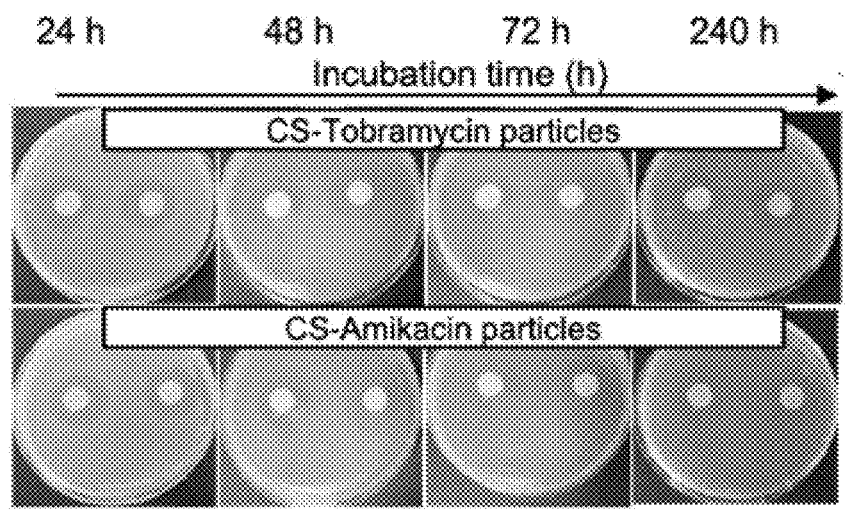
FIG. 12 depicts the inhibition zone (mm) drug loaded CS-Tobramycin 50% and CS-Amikacin particles 50% at 50 µL of 50 mg/mL concentration against *P. aeruginosa* at different incubation times.
Figure 13:
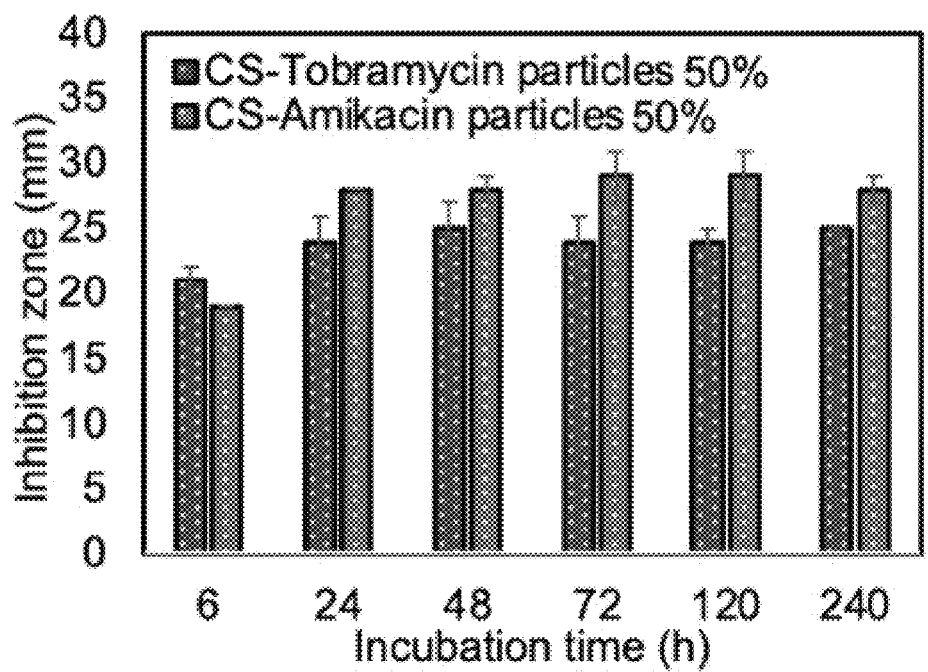
FIG. 13 depicts an analysis of the images in FIG. 12.

The drug loading of CS-tobramycin/amikacin particles for each formulation is 250 µg/mg with 100% entrapment efficiency. The high amounts of tobramycin and amikacin, about 250 µg/mg were loaded into the CS particle network by the encapsulation technique, and the release profiles of these drugs from CS-Tobramycin and CS-Amikacin particles crosslinked at 50, 40, and 20% mole ratios under physiological conditions at pH 7.4 and 37.5° C. are shown in FIGS. 8 and 9, respectively.

High amount of drug as 192±3 µg/mg of tobramycin or 214±2 µg/mg amikacin was quickly burst from the low crosslinked CS-Tobramycin/Amikacin particles with 20% crosslinking, for 24 h, because of fast degradable nature of CS particles crosslinked at 20%. Similarly, 215±8 µg/mg of tobramycin or 242±4 µg/mg amikacin was released from CS-Tobramycin and CS-Amikacin particles 40%, respectively within 72 h.

Sustainable release kinetics were observed within 150 h for both drugs and maximum 200±2 µg/mg of tobramycin and 228 µg/mg of amikacin were released cumulatively from the drug-loaded CS particles crosslinked at 50% over 240 h. The highest release profile was obtained for CS-Tobramycin/Amikacin particles prepared at 40% crosslinking due to the faster and more swelling ability of these particles in comparison to 50% crosslinked CS particles. These results indicate that release capacity of 50% crosslinked CS-Tobramycin particles was 80±0.8%, and CS-Amikacin particles could release 91±2% of the loaded drug within 240 h.

For bacterial ulcer treatments, almost 300 µg/100 µL concentration of antibiotic solution (2 drops) is generally recommended every 1 hour for severe infections for 1 day, followed by continuous applications every 4-8 hours per day. Almost similar drug doses could be administered with a single administration of 2.5 mg drug loaded CS particles crosslinked at 50% which release 500 µg tobramycin or 570 µg amikacin within 240 h. Thus, 50 µL of 50 mg/mL (2.5 mg) drug-loaded CS particles 50% were used for further antibacterial activity tests.

Antibacterial activities of CS-Tobramycin particles 50% and CS-Amikacin particles 50% were investigated by disc diffusion assay with 6 h to 240 h incubation times against *Pseudomonas aeruginosa* and tobramycin and amikacin drugs alone were used as control. Inhibition zone diameters for 20 µL of tobramycin and amikacin drugs between 2 and 50 mg/mL, which are equal to 40-1000 µg drugs, and 50 µL of 50 mg/mL CS-Tobramycin and CS-Amikacin particles 50% corresponding to 2.5 mg drug loaded CS particles loaded are illustrated in FIGS. 10, 11, 12, and 13.

According to the release study, nearly 277±13 µg of tobramycin and 322±14 µg of amikacin was released from 2.5 mg CS-Tobramycin and CS-Amikacin particles within 24 h, respectively. The inhibition zones for 2.5 mg CS-Tobramycin and CS-Amikacin particles after 24 h incubation was 24±2 mm and 28±0 mm, respectively, which are almost the same as the inhibition zones for 200 µg drug solutions determined as 25±1 mm. Antibacterial effects of CS-Tobramycin and CS-Amikacin particles remained the same for up to 240 h incubation time against *P. aeruginosa* because of sustainable release during the long-term period of 240 h.

Inhibition zone diameter, minimum inhibition concentration (MIC), and minimum bactericidal concentration (MBC) values of CS-Tobramycin and CS-Amikacin particles crosslinked at 50%, 40%, and 20% mole ratios were also determined against *P. aeruginosa* and listed below

| Drug carriers | Inhibition Zone (mm) | MIC (mg/mL) | MIC (mg/mL) |
| --- | --- | --- | --- |
| CS-Tobramycin particles 50% | 25 ± 1 | 0.375 | 1.500 |
| CS-Tobramycin particles 40% | 26 ± 1 | 0.375 | 0.750 |
| CS-Tobramycin particles 20% | 23 ± 2 | 0.750 | 1.500 |
| CS-Amikacin particles 50% | 28 ± 1 | 0.094 | 0.187 |
| CS-Amikacin particles 40% | 32 ± 2 | 0.046 | 0.046 |
| CS-Amikacin particles 20% | 26 ± 1 | 0.375 | 0.750 |

MIC values of CS-Tobramycin particles crosslinked at 50%, 40%, and 20% was determined as 0.375, 0.375, and 0.750 mg/mL, respectively. The antibacterial effects on the *P. aeruginosa* was dependent on the amount of release drug from the CS particle network and could be adjusted by changing crosslinker degree from the particle network. The highest antibacterial activity against *P. aeruginosa* was established in CS-Amikacin particles 40% with the lowest MIC and MBC value as 0.046 mg/mL and broadest inhibition zone as 32±2 mm with the highest drug release as 242±4

Wing amikacin. Both formulations could be used in the treatment of *Pseudomonas* keratitis because of the almost similar release profiles and high antibacterial effects. In the literature, essential oil loaded chitosan microcapsules embedded in biodegradable sodium alginate/gelatin hydrogels were used to eliminate *P. aeruginosa*, but the antibacterial effect of the hydrogels was very weak with a high concentration of MIC value at 39.3 mg/mL of cinnamon leaf oil as essential oil. In another study, amikacin loaded to gelatin coated poly(ethylene terephthalate) fibers were prepared and 15% of the loaded antibiotic were released within 7 days. The antibacterial activity of amikacin loaded fibers was found effectively for 7 days, but *P. aeruginosa* was growing back after 10 days. The low MIC values and long-term inhibition abilities of CS-Tobramycin/Amikacin particles make them highly promising materials for the treatment of bacterial infection in ocular applications.

Rosmarinic acid (RA) as a therapeutic agent was loaded into CS microgels and CS$^-$[NH$_4$]$^+$ microgels by adsorption technique. Briefly, 0.03 g of RA was dissolved in 30 mL of 1:1 volume ratio of ethanol:water solution and 0.15 g of CS-based microgels were added into RA solution containing container. For loading process, this microgel suspension was stirred at 300 rpm for 6 h. After this period, the microgels were washed with 1:1 volume of ethanol-water mixture by centrifugation at 10,000 rpm for 10 min and dried by freeze-dryer. The RA loading amounts were determined from the absorbance of the drug solution before and after the loading process by using UV-VIS spectroscopy (T80+PG Instrument) at 325 nm against the previously created corresponding calibration curves of RA prepared in ethanol-water mixture.

In drug release study, 50 mg of RA loaded CS microgels and/or CS$^-$[NH$_4$]$^+$ microgels were dispersed in 1 mL of phosphate buffer saline (PBS) at pH 7.4 and transferred to a dialysis membrane. This particle containing membrane was placed into 20 mL of PBS solution at 37° C. in a shaker bath. The drug releasing medium, PBS solution, was then sampled and evaluated by UV-Vis spectrometer (T80+PG Instrument) at 325 nm to measure the amount of RA against the previously determined corresponding RA calibration curves prepared in PBS, and the released amounts of RA were calculated. The analysis was repeated three times, and the values are reported as the average values with standard deviations.

Figure 26:
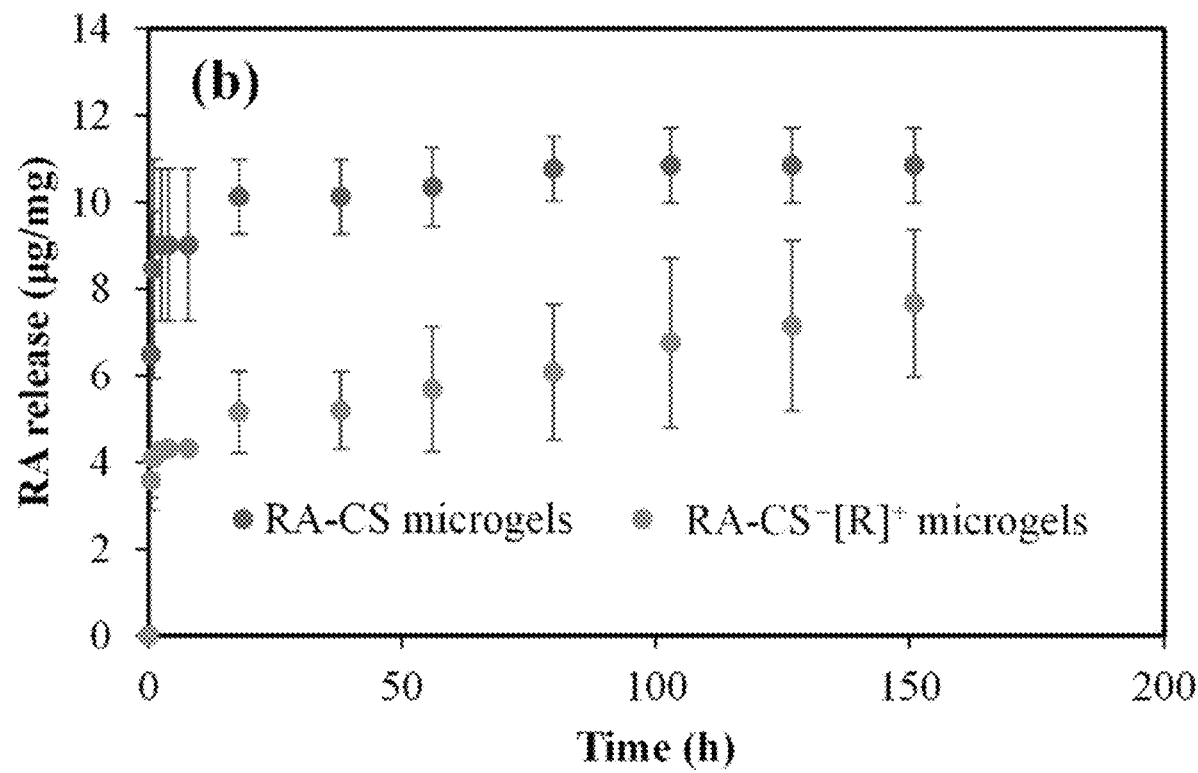
FIG. 26 depicts RA release profiles of CS and polyelectrolyte $CS^-[R]^+$ microgels at physiological condition, pH 7.4 (PBS) and 37° C.

RA release profiles from RA-CS microgels and RA-CS$^-$[NH$_4$]$^+$ microgels at physiological condition, pH 7.4 (PBS) and 37° C. was illustrated in FIG. 26. RA-CS microgels exhibit burst RA delivery within 20 h with 10.8±0.8 µg/mg RA delivery, whereas 7.6±1.7 µg/mg RA was linearly released from RA-CS$^-$[NH$_4$]$^+$ microgels. The RA release capacity of polyelectrolyte form of CS microgels was significantly decreased compare with CS microgels, but sustainable and long-term RA delivery was provided for 150 h.

Total phenolic content of the particles was evaluated by Folin-Ciocalteau (FC) method. Briefly, 0.1 mL of 1 mg/mL microgel suspensions were reacted with 1.25 mL of 0.2 N solution of FC phenol reagent for 4 min. Next, 1 mL of 0.7 M sodium bicarbonate solution was added to this mixture and kept in the dark for 2 hours. Then, the total phenol content of the microgels was measured by using a UV/Vis spectrophotometer (T80+PG Instrument) at 760 nm. The antioxidant activity of the microgels was expressed as µg/mL gallic acid equivalent. The analysis was repeated three times, and the values are reported as the average values with standard deviations.

The antioxidant capacity of bare and RA loaded CS microgels and CS$^-$[NH$_4$]$^+$ microgels and RA were evaluated by the ABTS scavenging assay. The ABTS radical solution was prepared by mixing 2.45 mM 2.5 mL of potassium persulfate and 7 mM 7.5 mL ABTS solution in DI water; the mixture was kept in the dark for 12 h at 4° C. to obtain stock ABTS·$^+$ solution. This stock ABTS·$^+$ solution was diluted with PBS to adjust an absorbance of 0.7±0.05 at 734 nm using a UV-Vis spectrophotometer (T80+PG Instrument). Then, 1 mg/mL concentration of each microgel suspension was prepared in 5 mL of PBS solution and various amounts of this suspension from 200 to 500 µL were reacted with 3000 µL of ABTS·$^+$ solution for 6 min. Separately, 0.1 mg/mL concentration of RA solution in PBS was prepared and 25-75 µL of this solution was interacted with 3000 µL of ABTS·$^+$ solution for 6 min. At the end of this time, the decrease in absorbance value was detected at 734 nm. The antioxidant materials were determined for the values of 20-80% reduction of the blank absorbance. Trolox equivalent antioxidant capacity (TEAC) values were determined against the slope of a trolox standard curves and expressed as "µmol trolox equivalent/g". The analysis was repeated three times, and the values are reported as the average values with standard deviations.

2,2-Diphenyl-1-picrylhydrazine assay (DPPH) solution was prepared in ethanol at 100 µM concentration. Then, 10 mg of CS, CS$^-$[NH$_4$]$^+$, RA loaded CS and RA loaded CS$^-$[NH$_4$]$^+$ microgels was added to 3 mL of DPPH solution and incubated for 1 h in the dark environment. The absorbance of DPPH solution was measured at 517 nm. The radical scavenging activity % was determined as a decrease in the absorbance of DPPH by the following equation:

$$\text{DPPH radical scavenging activity \%} = (A_{control} - A_{sample})/A_{control} \times 100$$

$A_{sample}$ is the absorbance of the sample and $A_{control}$ is the absorbance of the blank (without sample).

Figure 27:
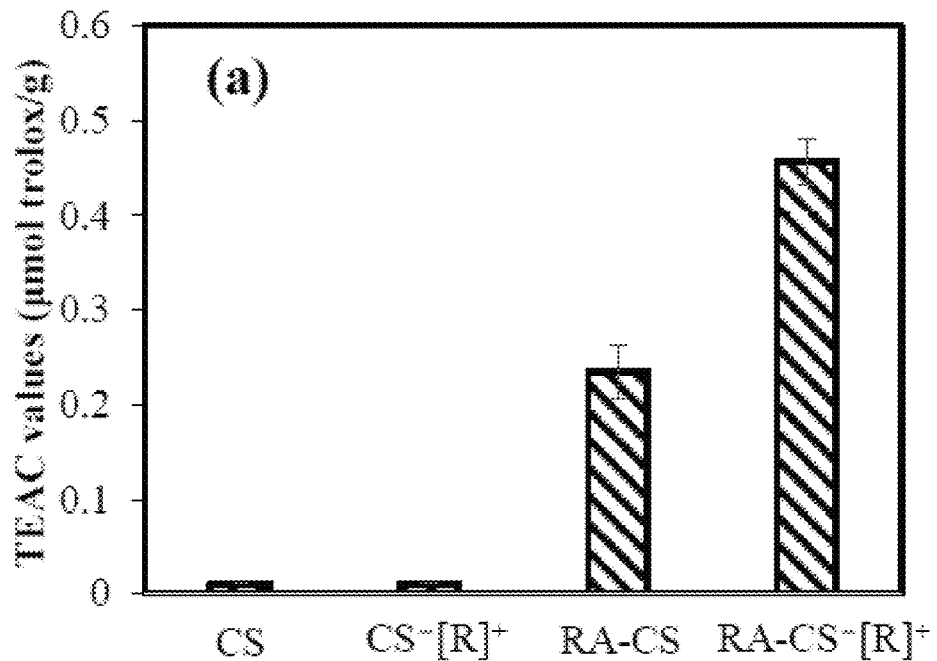
FIG. 27 depicts the antioxidant capacity of bare and RA loaded CS microgels and polyelectrolyte $CS^-[R]^+$ microgels via 4hile4 equivalent antioxidant capacity (TEAC) test.
Figure 28:
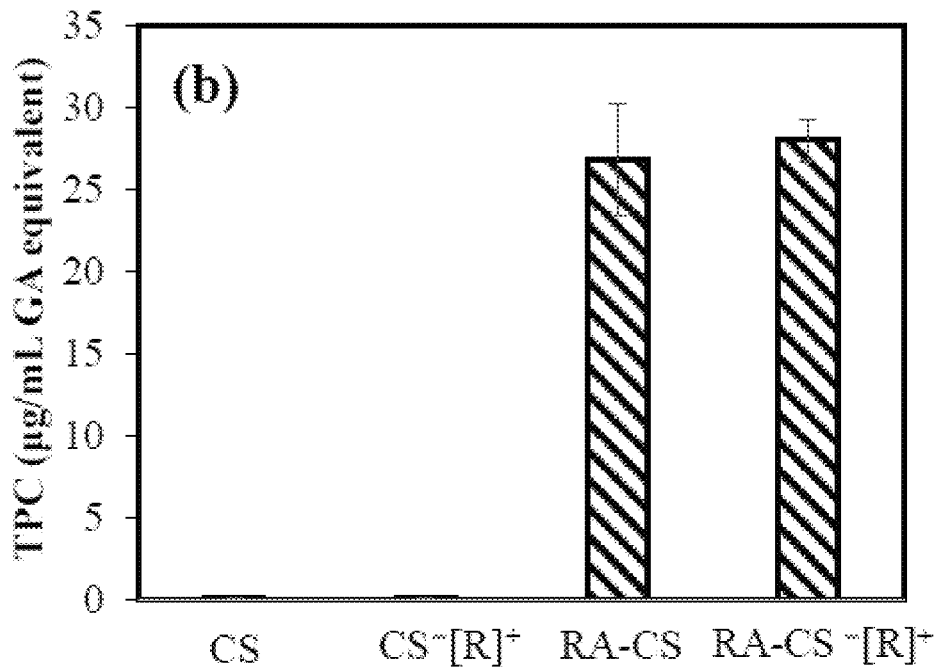
FIG. 28 depicts the antioxidant capacity of bare and RA loaded CS microgels and polyelectrolyte $CS^-[R]^+$ microgels via gallic acid (GA) equivalent total phenol content (TPC) at 1000 µg/mL concentration of microgels.
Figure 29:
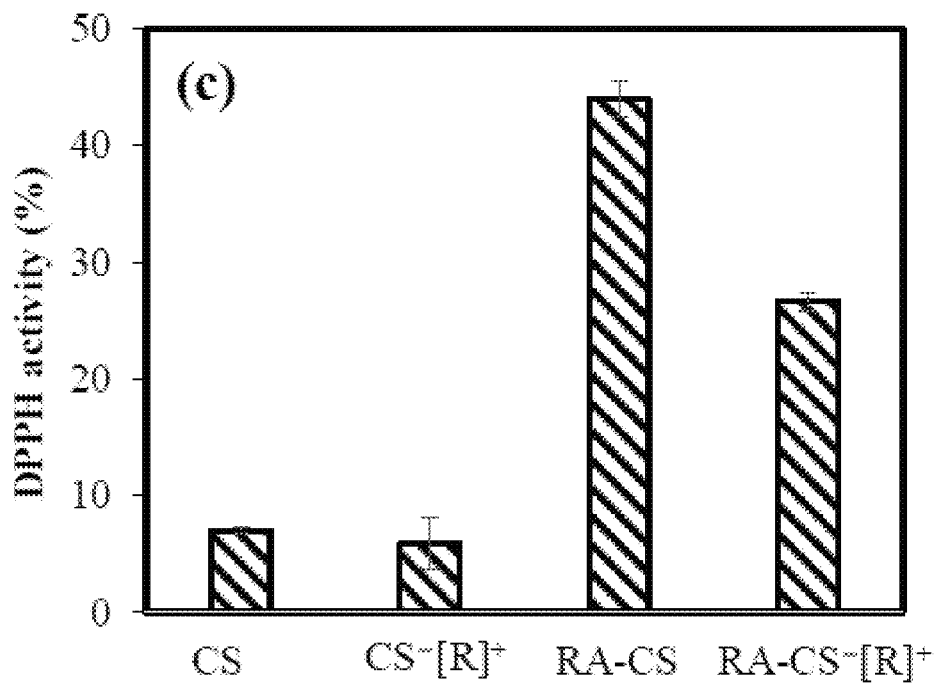
FIG. 29 depicts the antioxidant capacity of bare and RA loaded CS microgels and polyelectrolyte $CS^-[R]^+$ microgels via DPPH radical scavenging assay for 3.33 mg/mL concentration of the microgels.

The antioxidant activity of bare and RA loaded CS microgels and CS$^-$[NH$_4$]$^+$ microgels were investigated by ABTS scavenging, FC, and DPPH scavenging assays as represented in FIGS. 27, 28, and 29, respectively. In the ABTS radical scavenging test, no antioxidant effect was found for bare microgels, but 0.23±0.03 and 0.45±0.02 µmol/g 39hi1e39 equivalent antioxidant capacity (TEAC) values were measured for RA loaded CS microgels and CS$^-$[NH$_4$]$^+$ microgels, respectively. As a control, TEAC value of only RA was determined as 10.32±1.01 mol/g. In the other antioxidant test, total phenol content (TPC) of RA loaded CS microgels and CS$^-$[NH$_4$]$^+$ microgels at 1000 µg/mL concentration were demonstrated antioxidant capacity of 26.8±3.4 and 28.0±1.3 µg/mL gallic acid equivalent, respectively. Only RA at the same concentration has 556±35 µg/mL gallic acid equivalent TPC value. These results confirm that RA loaded CS$^-$[NH$_4$]$^+$ microgels show great antioxidant ability with almost 20-fold lesser antioxidant capacity of sole RA. In the DPPH scavenging activity test, the inhibition % of 3.33 mg/mL concentration of bare CS microgels and CS$^-$[NH$_4$]$^+$ microgels were measured as 7.0±0.2 and 5.9±2.2%. On the other hand, the same amount of RA loaded CS microgels and CS$^-$[NH$_4$]$^+$ microgels show higher scavenging ability with 44.0±1.5 and 26.6±0.7% DPPH inhibition activity in about 30 min. $IC_{50}$ value of RA, which defined as the concentration of 50% inhibition of DPPH radical was reported as 1.3±0.1 µg/mL. The highest antioxidant ability in the DPPH assay was determined for CS-RA microgels with almost 3.33 mg/mL of $IC_{50}$ value.

Figure 22:
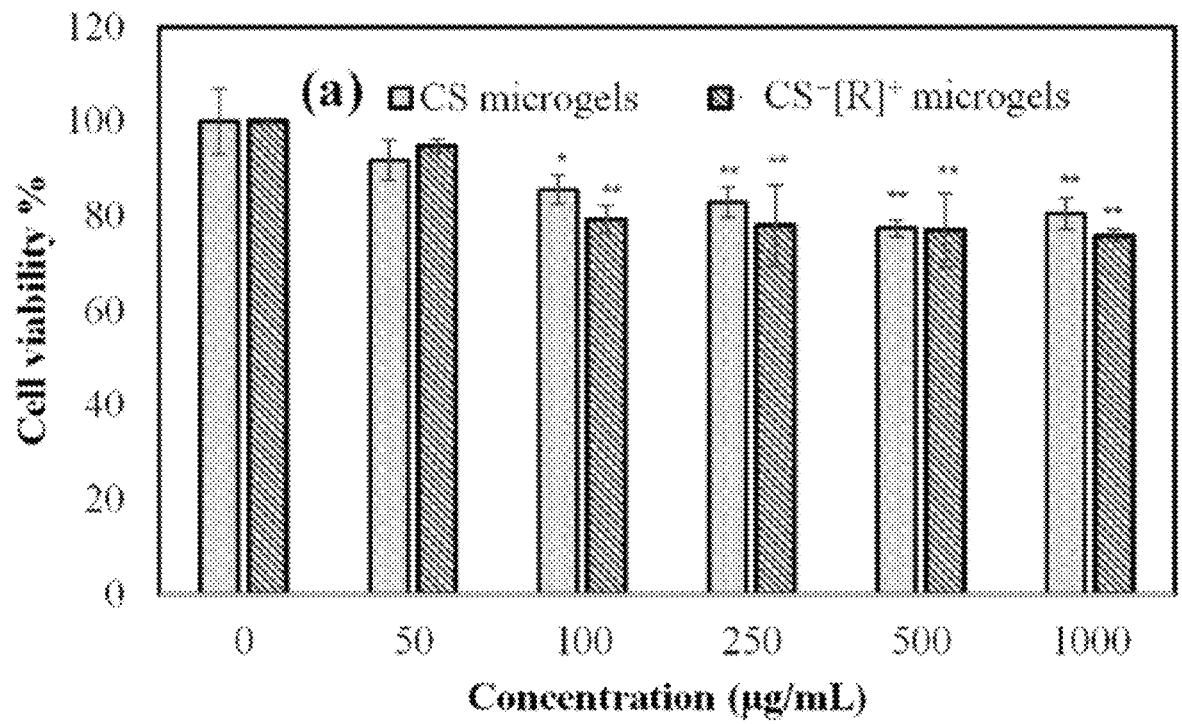
FIG. 22 depicts the cell viability of L929 fibroblasts in the presence of different concentration of CS and $CS^-[R]^+$ microgel.
Figure 23:
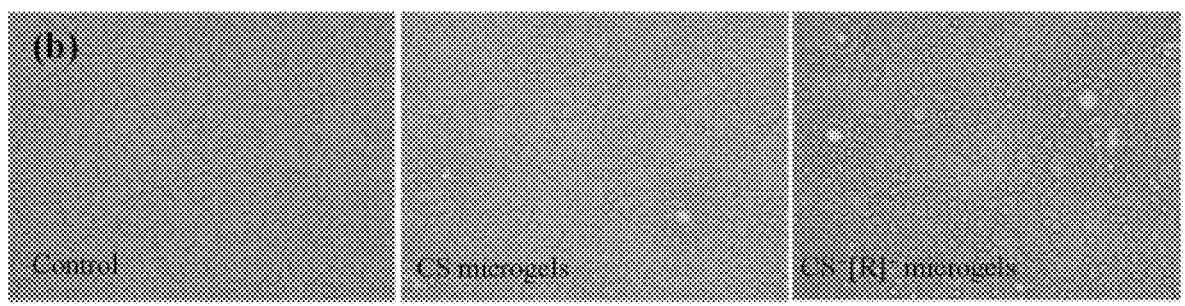
FIG. 23 depicts optic microscope images of the L929 fibroblast cells for control groups and 1000 m/mL concentration of CS microgel and $CS^-[R]^+$ microgel.
Figure 24:
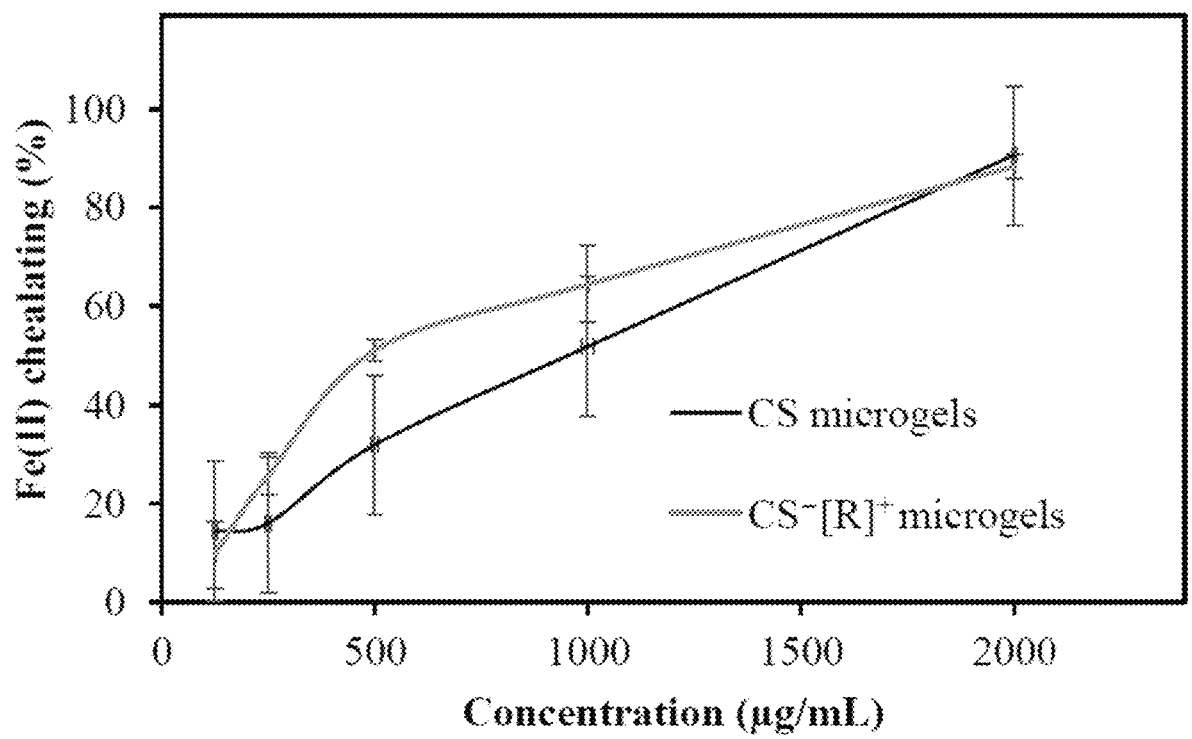
FIG. 24 depicts Fe(II) chelating activities of CS microgels and polyelectrolyte $CS^-[R]^+$ microgels.
Figure 25:
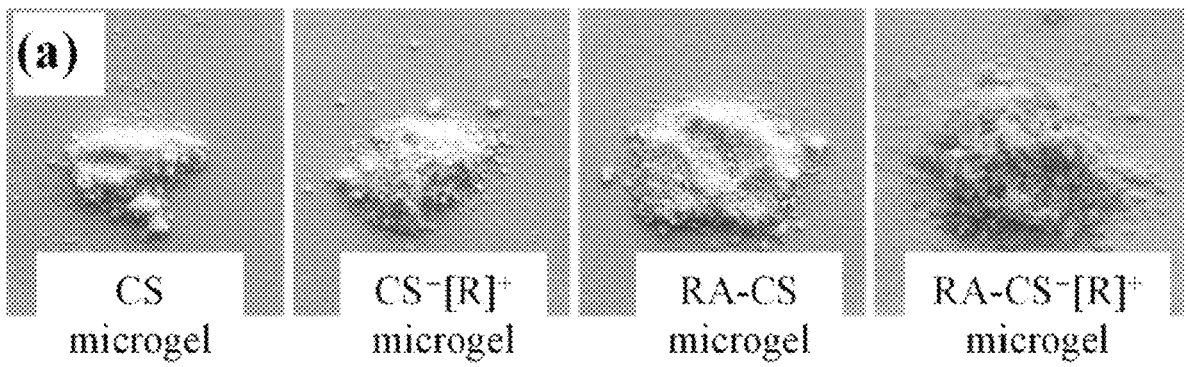
FIG. 25 depicts digital camera images of CS microgels and $CS^-[R]^+$ microgels and their RA loaded forms.

CS microgels and CS⁻[NH₄]⁺ microgels aqueous solutions were prepared at 2000 µg/mL concentrations and diluted to 1000, 500, 250, 125 µg/mL. Then, 140 µl of CS microgels or CS⁻[NH₄]⁺ microgels suspension solution was put into 96 wells. Then, 20 µl of 1 mM of Fe(II) aqueous solution was added to them, and measurements were made using a microplate reader (Thermo Multiskan Go) at 562 nm. Finally, 40 µl of 2.5 mM ferrozine aqueous solution was added and the measurement was made again. Pure water was used for control. The results were calculated according to the literature. As shown in FIGS. 22, 23, and 24 CS had Fe(II) chelating capacity of 51.8±15.8%, while CS⁻[NH₄]⁺ microgels was increased to 64.5±7.7% at the concentration of 1000 µg/mL due to the highly electrolyte nature of the microgels.

Iron chelators can be used as a therapeutic agent in several neurological diseases. As shown as FIG. 24, it was observed that the Fe(II) chelating capacity of CS microgels and CS–[R]+ microgels increased depending on the concentration.

Example 3: Biocompatibility of Chondroitin Sulfate Particles

Hemolysis and blood clotting assays were performed to investigate the hemocompatibility of CS-based particles. Human blood was obtained from healthy volunteers and approved by the Clinical Research Ethics Committee of Canakkale Onsekiz Mart University (2011-KAEK-27/2022) and placed into tubes containing EDTA. Before the analysis, all solutions were preheated to 37° C.

For the hemolysis assay, diluted blood was prepared by using 1:1.25 (v:v) ratio of blood:0.9% aqueous NaCl solution and 200 µL of the diluted blood was interacted with CS-based particle suspensions in 10 mL of 0.9% saline solution at 100, 250, 500, and 1000 µg/mL concentrations in a water bath at 37° C. for 1 h. In the separation tubes, 200 µL of the diluted blood was added into 10 mL of 0.9% aqueous NaCl solution with DI water as a negative and positive control, respectively. Then, the tubes were centrifuged at 100 g for five minutes and the absorbance values for the supernatants were measured at 542 nm with UV-Vis spectroscopy (T80+UV/VIS spectrometer, PG Instrument Ltd. Leicestershire, UK). The hemolysis ratio of the CS-based particles was evaluated using the equation:

$$\text{Hemolysis ratio \%} = (A_{material} - A_{negative})/(A_{positive} - A_{negative}) \times 100$$

where $A_{material}$ is the absorbance value of the blood solution interacted with materials in 0.9% aqueous NaCl solution. $A_{negative}$ and $A_{positive}$ are the absorbance values of the blood solution without materials in 0.9% aqueous NaCl solution and in DI water, respectively. All assays were carried out in triplicate and the results are given with standard deviations.

For the blood clotting assay, 80 µL of 0.2 M CaCl₂ aqueous solution was mixed with 1 mL of blood containing EDTA and immediately 270 µL of this blood was covered with 1, 2.5, 5, and 10 mg of the CS-based particles placed into the tubes. After 10 min, 10 mL of DI water was slowly added into the tubes and centrifuged at 100 g for 1 minute. Then 10 mL of supernatant solution containing non-clotting blood was taken from the tube and diluted with 40 mL of DI water. In the separation tube, 250 µL of the blood containing EDTA was dispersed in 50 mL of DI water as a control. The blood solution was incubated at 37.5° C. in a water bath for 1 h and then, the absorbance value of the supernatant was measured at 542 nm by using UV-Vis spectroscopy. The blood clotting index of the CS-based particles was evaluated from the equation:

$$\text{Blood Clotting Index} = (A_{material} - A_{control}) \times 100$$

where $A_{material}$ is the absorbance value of the blood solution interacted with the CS-based particles and $A_{control}$ is the absorbance value of the blood solution without the CS-based particles as a control. All assays were carried out in triplicate and the results are given with standard deviations.

Figure 14:
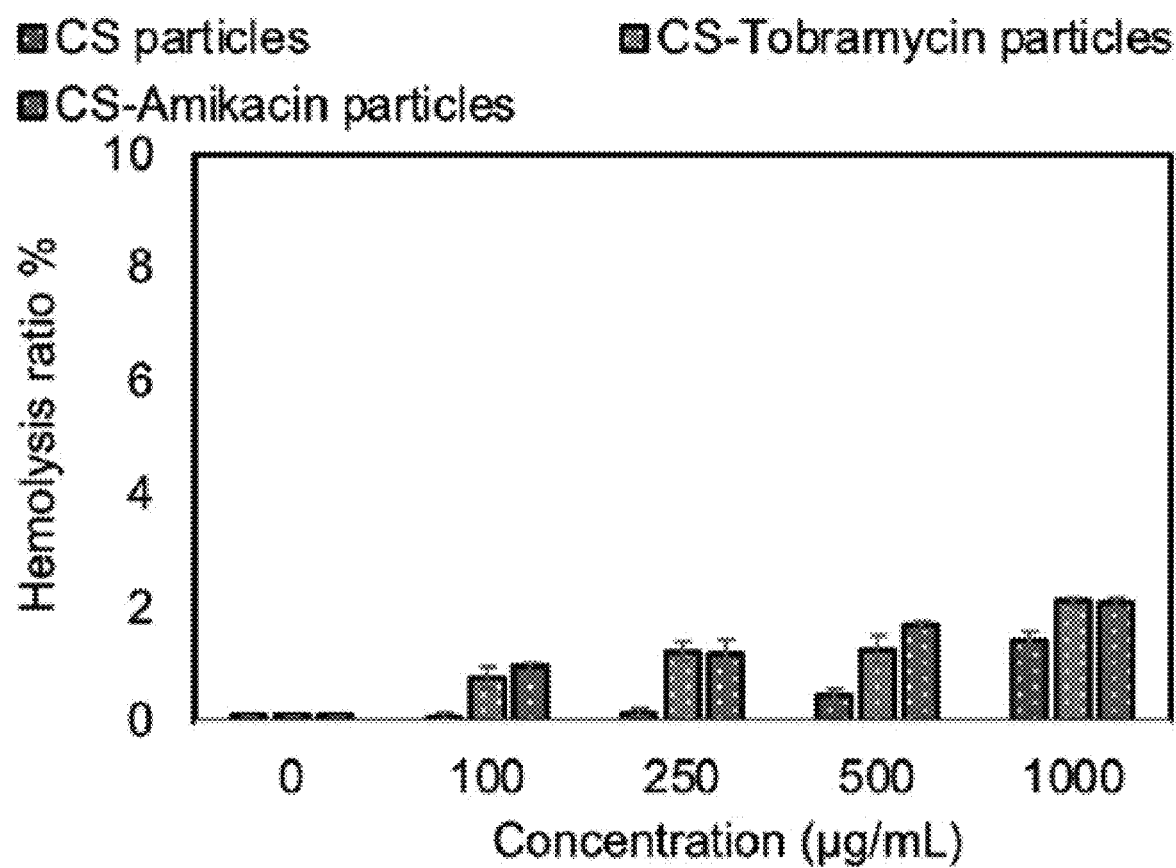
FIG. 14 depicts the hemolysis index of CS particles, CS-Tobramycin particles and CS-Amikacin particles crosslinked at 50% mole ratios.

Blood compatibility of biomaterials is an important parameter for intravascular applications. Hemolysis ratio and blood clotting index of non-degradable CS particles and drug-loaded forms of CS-Tobramycin and CS-Amikacin were determined for various concentrations of CS-based particles from 100 to 1000 µg/mL. As can be seen in FIG. 14, CS particles were found non-hemolytic materials with acceptable 1.4±0.2% hemolysis ratio even at 1000 µg/mL concentration, whereas CS-Tobramycin and CS-Amikacin particles were found to possess slightly more hemolytic materials (in comparison to CS-Tobramycin) at 1000 µg/mL concentration with 2.1±0.1% and 2.0±0.1% hemolysis ratio values.

Figure 15:
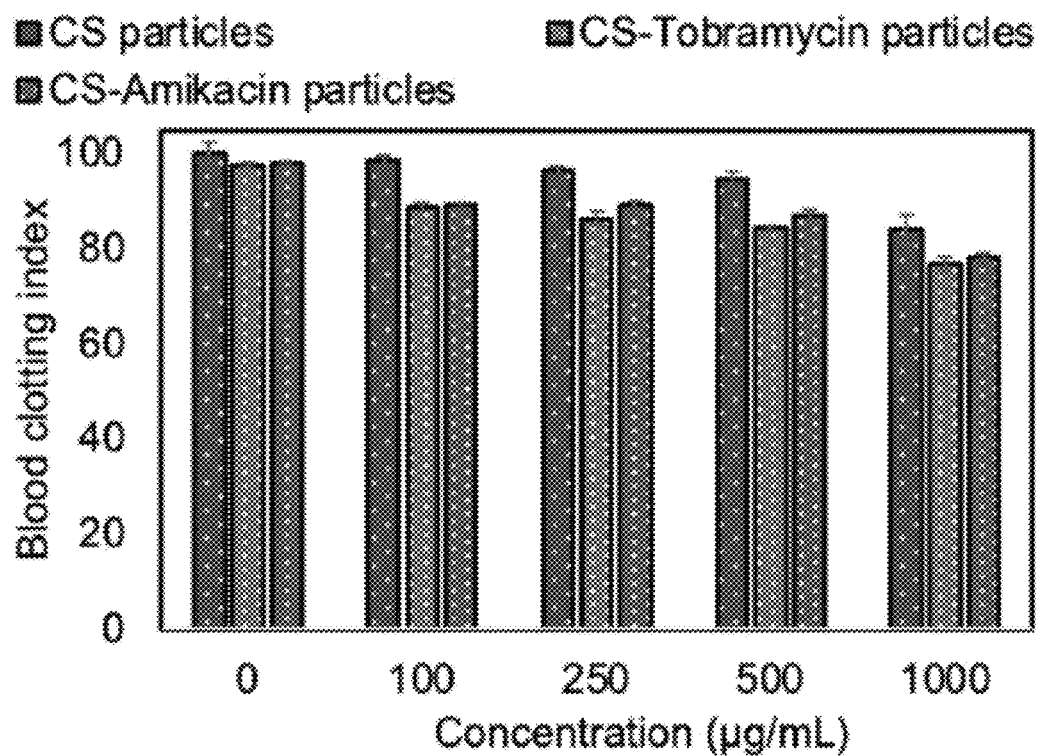
FIG. 15 depicts the blood clotting index of CS particles, CS-Tobramycin particles and CS-Amikacin particles crosslinked at 50% mole ratios.
Figure 16:
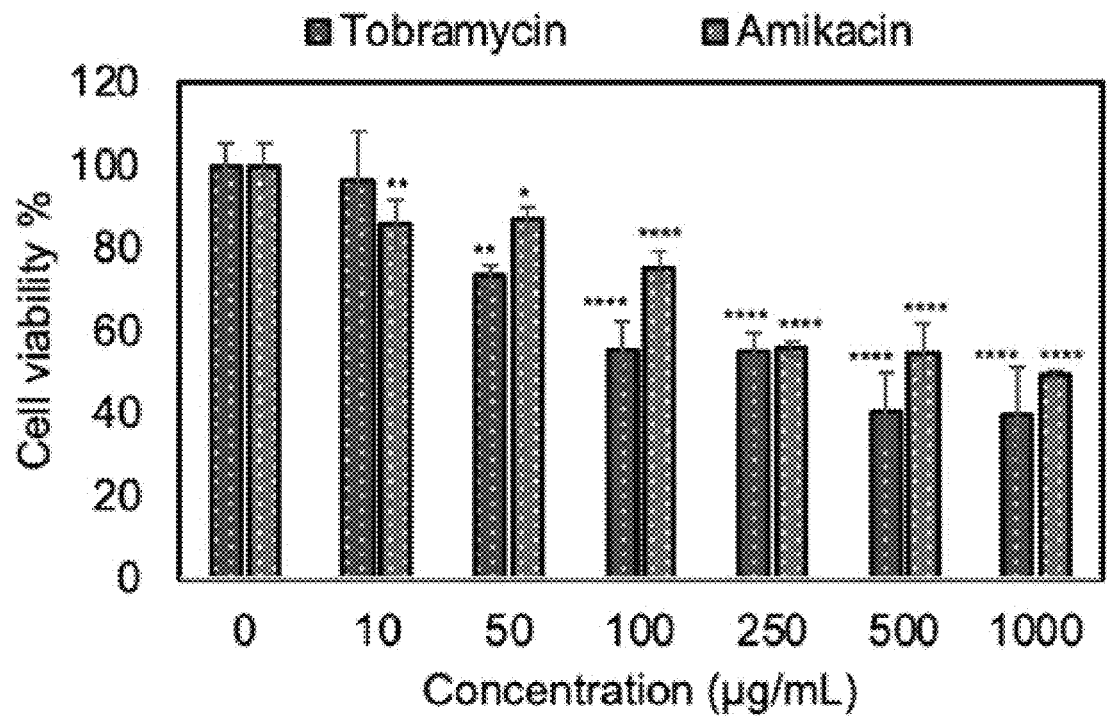
FIG. 16 depicts the cell viability when treated with tobramycin and amikacin in the absence of CS particles.

Consequently, these particles were non-hemolytic at 500 µg/mL concentration with 1.3±0.2% and 1.7±0.1% hemolysis ratio values, respectively. Similarly, CS particles were blood compatible with a high blood clotting index of 94.4±1.7 at 500 µg/mL concentration. The blood clotting index of CS-Tobramycin and CS-Amikacin particles decreased to 87.1±0.9 and 84.4±0.6 values for 500 µg/mL concentrations of the particles as seen in FIG. 15. These results show that hemo-compatible bare and drug-loaded CS particles can be used directly with up to 500 µg/mL high concentration for safe intravascular applications. Some patients may use to require high doses of tobramycin and amikacin drugs for a long time to fight keratitis due to *P. aeruginosa* ulcers. Cytotoxicity of tobramycin and amikacin drugs alone on L929 fibroblast cells were analyzed at different concentrations between 10 and 1000 µg/mL for 24 h incubation time as shown in FIG. 16.

For cytotoxicity analysis, L929 fibroblast cells were cultured under 5% CO₂ atmosphere in an air-humidified incubator in DMEM supplemented with 10% FBS and 100 U/mL penicillin-streptomycin at up to 80% confluency. The cell viability % of the fibroblasts in the presence of study materials was analyzed by MTT colorimetric assay which measures the healthy cells which form formazan crystals via cleavage of the tetrazolium ring of the MTT agent. The L929 fibroblast cells at a density of 5×10⁵ cells per mL were suspended in 10 mL of culture media and 100 µL of this cell suspension was seeded onto wells on a 96-well plate. The plate was incubated at 37° C. under 5% CO₂ in an air-humidified incubator for 24 h. After adherence of the fibroblasts, the culture medium was removed from the wells and 100 µL of drug solution or CS-based particle suspension in culture medium at different concentrations between 50 and 1000 µg/mL was added to the cells. The plate was incubated at 37° C. under 5% CO₂ in an air-humidified incubator for 24 h more. Only culture medium was used as a control group accepted as 100% viability. At the end of the incubation, the medium was removed from the wells, the cells were washed with PBS at pH 7.4, and 100 µL 0.25 mg/mL concentration of MTT agent diluted in culture medium was added to each well. The plate was incubated at room temperature in the dark for 2 h. Then, MTT solution was removed from the wells and 200 µL of DMSO was placed into the wells to dissolve the formazan crystals. The absorbance of the wells was measured at 590 nm with a plate reader (HEALES, MB-530, Shenzhen, China). The absorbance value of control group was accepted as 100% viability and the decrease in cell viability % was estimated based on the absorbance values of the wells treated with study material by following equation:

$$\text{Cell viability \%} = (A_{material}/A_{control}) \times 100$$

where $A_{material}$ is the absorbance value of the cells interacting with materials and $A_{control}$ is the absorbance value of the untreated cells as control. All assays were carried out in triplicate and the results are given with standard deviation.

Figure 17:
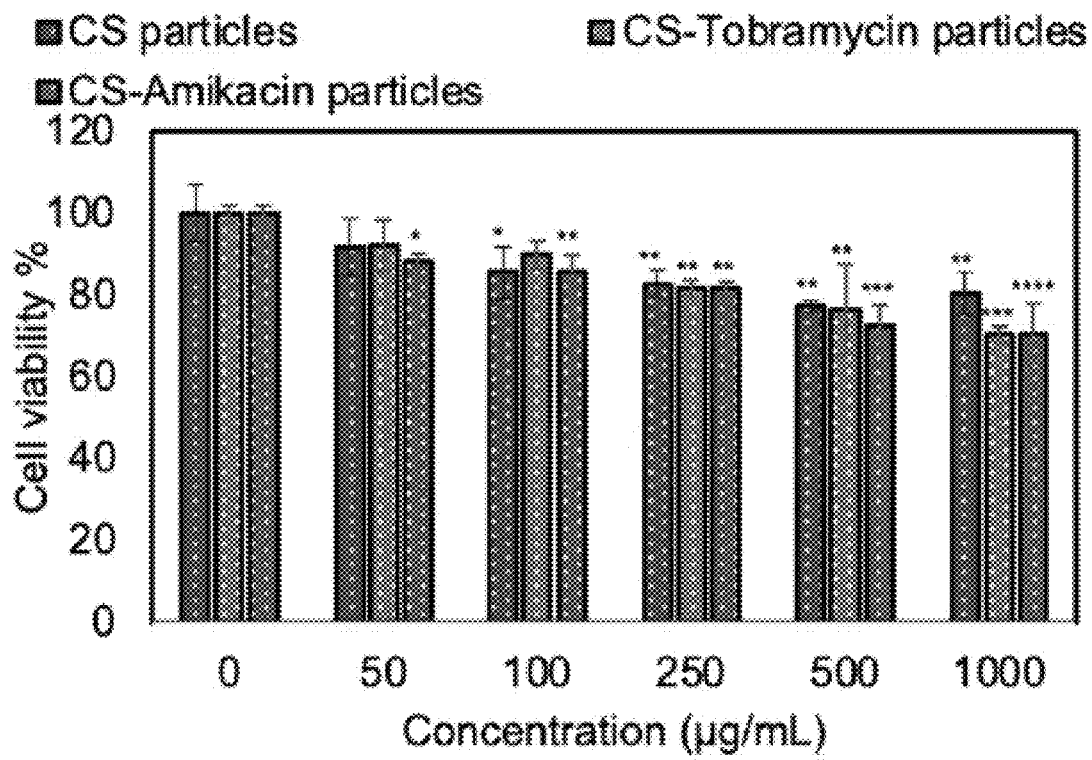
FIG. 17 depicts the cell viability of CS particles, CS-Tobramycin particles and CS-Amikacin particles cross-linked at 50% mole ratios.
Figure 18:
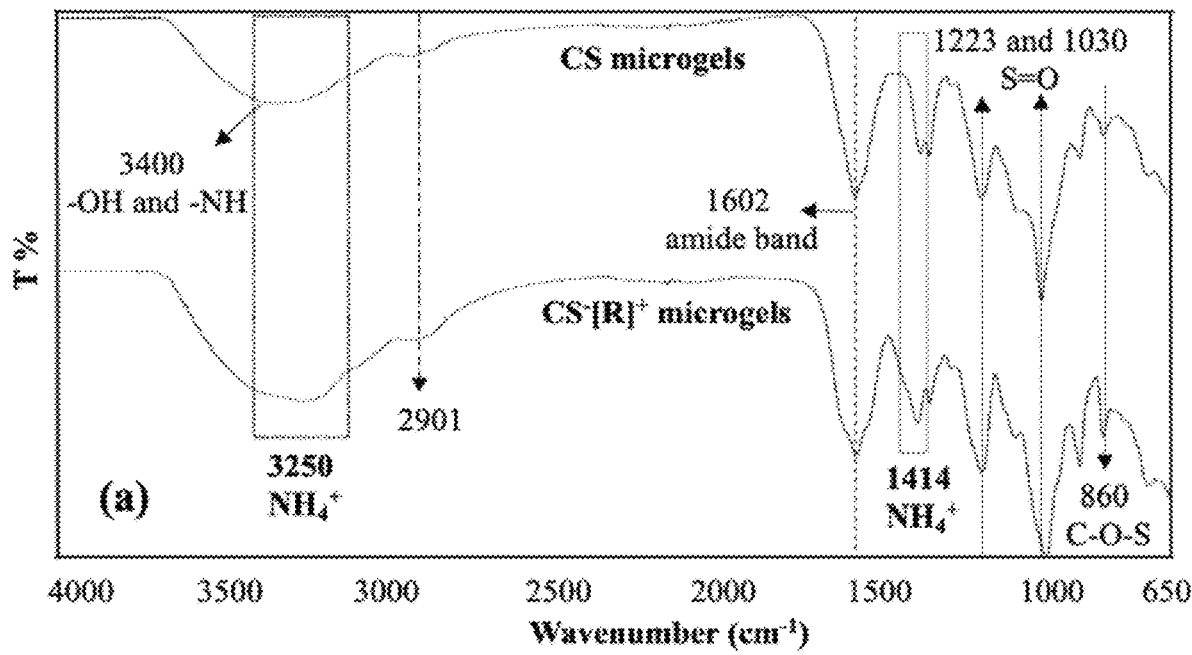
FIG. 18 depicts the FT-IR spectra of CS microgels and polyelectrolyte $CS^-[R]^+$ microgel (unless specified to the contrary, $CS^-[R]^+$ is the same as $CS^-[NH_4]^+$).
Figure 19:
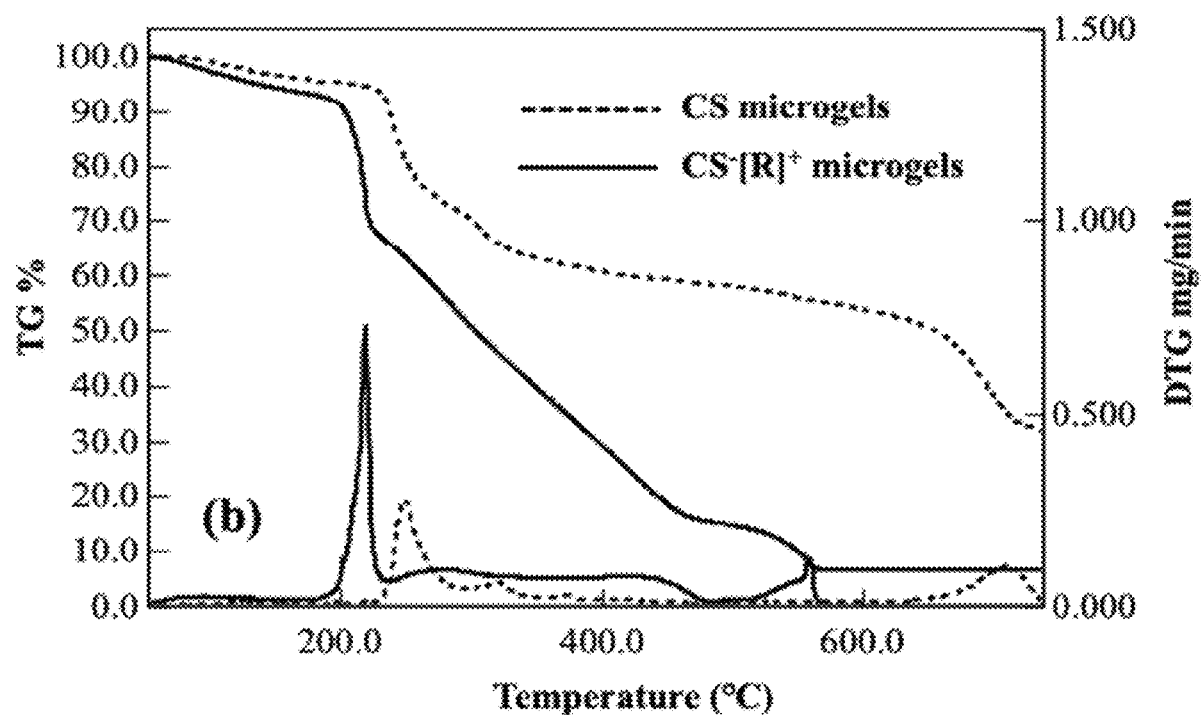
FIG. 19 depicts the thermogravimetric/differential thermogravimetric (TG/DTG) analysis curves of CS microgels and polyelectrolyte $CS^-[NH_4]^+$ microgels.

The cytotoxicity of bare CS particles and drug-loaded CS-Tobramycin and CS-Amikacin particles was also determined by direct contact with L929 fibroblast culture. The proliferation of the fibroblasts in the presence of CS-based particles at different concentrations was shown in FIG. 17. At particle concentrations of 1000 µg/mL, the cell viability percentage were slightly decreased to 80±5%, 71±2%, and 71±7% for CS particles, CS-Tobramycin particles, and CS-Amikacin particles, respectively. 1000 µg of drug-loaded CS particles could release more than 100 µg of drugs such as tobramycin or amikacin within 24 h. According to the cytotoxicity results, concentrations of 100 µg/mL or above of tobramycin or amikacin drugs destroyed the fibroblast cells with less than 60% cell viability. The drug-loaded CS-Tobramycin and CS-Amikacin particles were found to be much more biocompatible, with no significant cell loss up to 250 µg/mL concentration with more than 80% cell viability values.

CS microgels and CS⁻[NH₄]⁺ microgels were suspended in DMEM in order to obtain an initial concentration of 1000 µg/mL. This sample was adjusted to 500, 250, 100 and 50 m/mL concentrations by diluting with DMEM solution. The stock L929 fibroblast cell cultures were seeded in 96-well plates with approximately $1 \times 10^5$ cells for each well in 0.1 mL of DMEM culture medium and the plate incubated in a 5% $CO_2$ 95% air atmosphere at 37° C. for 24 hours. After the incubation time, the media in the well were removed and various concentrations from 1000 m/mL to 50 m/mL particle suspension in 100 µL DMEM medium were added on the attached cells into the wells and incubated for 24 hours. For positive control, only 100 µL DMEM was added in the wells. Following the incubation period, the culture media was removed, and cells were washed with phosphate-buffered solution (PBS). Then, 5 mg/mL of MTT agent was diluted 10-fold in DMEM and 100 µL of this agent solution was added to the each well. The 96-well plate was kept in dark for 2 hours. Finally, the media was discarded and 200 µL of DMSO was added to each well to dissolve of the formazan crystals and absorbance values at 590 nm were read by using a microplate reader (HEALES, MB-530). The analysis was repeated three times, and the values are reported as the average values with standard deviations.

Cell viability % of the fibroblasts in the presence of CS microgels and polyelectrolyte CS⁻[NH₄]⁺ microgels even at a high concentration i.e., 1000 µg/mL were found as 81±5%, and 76±1%, respectively. Cell viability of both CS based microgels were almost similar and not significantly decreased up to 1000 µg/mL concentration. Moreover, cell image of control and cell images after incubating with 1000 µg/mL concentration of CS microgels or CS⁻[NH₄]⁺ microgels for 24 h reveal that the cells interacted with both types of CS based microgels were healthy and revealed the almost similar cell viabilities with control group. Therefore, it could be said that polyelectrolyte CS⁻[NH₄]⁺ microgels are biocompatible against fibroblast cells and can be safety used for further in vivo applications <1000 µg/mL concentration.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, 44hilee only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A composition, comprising:
   divinylsulfone-crosslinked chondroitin sulfate particles; and
   at least one active agent encapsulated within the crosslinked chondroitin sulfate particles,
   wherein the crosslinked chondroitin sulfate is a crosslinked chondroitin sulfate polyelectrolyte with a pH of 4-10 comprising a cationic counterion that is ammonium, wherein at least 50% of the cationic counterions are ammonium.

2. The composition according to claim 1, wherein the crosslinked chondroitin sulfate particles have an average particle from 500-2,000 nm.

3. The composition according to claim 1, wherein the crosslinked chondroitin sulfate particles have a crosslinking ratio from 40-60%.

4. The composition according to claim 1, wherein the active agent comprises one or more of analgesic agents, anti-anxiety agents, anti-arthritic agents, antibiotic agents, anticancer agents, anticholinergic agents, anticonvulsants, antidepressants, antidiabetic agents, antidiarrheal agents, anti-emetic agents, antihistamines, antihyperlipidemic agents, antifungal agents, anti-parasitic agents, anti-inflammatory agents, antimigraine agents, anti-obesity agents, antioxidants, antipruritic agents, antipsychotic agents, antispasmodic agents, antiviral agent, contraceptive agents, diuretic agents, hormones, anti-hormones, immunosuppressive agents, leukotriene inhibitors, narcotic agonists, narcotic antagonists, neurotransmitters, nicotine, nucleic acids, peptide drugs, thrombolytic agents, vasodilators, or a combination of distinct agents thereof.

5. The composition according to claim 1, wherein the active agent comprises an antifungal, antibiotic, antiviral, anti-parasitic, or a combination of distinct agents thereof.

6. The composition according to claim 1, wherein the active agent comprises an antibiotic.

7. The composition according to claim 1, wherein the active agent comprises an antioxidant.

8. The composition according to claim 1, wherein the crosslinked chondroitin sulfate comprises the active agent in an amount from 10-5,000 µg active agent per 1 mg crosslinked chondroitin sulfate.

9. The composition according to claim 1, wherein the crosslinked chondroitin sulfate particles have polydispersity from 0.1-0.8.

10. The composition according to claim 1, further comprising an aqueous vehicle.

11. A method of preparing a crosslinked chondroitin sulfate of claim 1, comprising the steps:
   a) preparing an inverse emulsion comprising an alkaline solution of uncrosslinked chondroitin sulfate;
   b) mixing the inverse emulsion with a crosslinking agent to prepare crosslinked chondroitin sulfate; and
   combining the crosslink chondroitin sulfate with a nitrogenous base, wherein the nitrogenous base comprise ammonia.

12. The composition according to claim 11, wherein the crosslinking agent is combined with one or more active agents, and said combination is mixed with the inverse emulsion.

13. The composition according to claim 11, wherein the inverse emulsion comprises at least one active agent prior to mixing with the crosslinking agent.

14. The composition according to claim 11, wherein the uncrosslinked chondroitin sulfate has an average molecular weight from 10,000-50,000 Da.

15. A method of treating an infection in a subject in need thereof, comprising administering to the subject the composition according to claim 1, wherein the active agent comprises an anti-infective agent.

16. The method according to claim 15, wherein the infection comprises a bacterial infection.

17. The method according to claim 15, wherein the composition is topically administered to the subject.

18. The method of claim 16, wherein the composition is ocularly administered to the subject.

* * * * *